United States Patent
Condie et al.

(10) Patent No.: US 12,150,703 B2
(45) Date of Patent: Nov. 26, 2024

(54) MICROWAVE ABLATION SYSTEMS AND METHODS HAVING ADJUSTABLE ABLATION PARAMETERS AND MODES OF OPERATION

(71) Applicant: Biocompatibles UK Limited, Camberley (GB)

(72) Inventors: Catherine Condie, Shoreview, MN (US); Daniel T. Kollman, Andover, MN (US); Megan Spitzer, Minneapolis, MN (US); Oleg F. Mosesov, Maple Grove, MN (US)

(73) Assignee: Biocompatibles UK Limited (GB)

( * ) Notice: Subject to any disclaimer, the term of this patent is extended or adjusted under 35 U.S.C. 154(b) by 400 days.

(21) Appl. No.: 17/145,304

(22) Filed: Jan. 9, 2021

(65) Prior Publication Data
US 2021/0212763 A1     Jul. 15, 2021

Related U.S. Application Data

(60) Provisional application No. 62/959,573, filed on Jan. 10, 2020.

(51) Int. Cl.
*A61B 18/18* (2006.01)
*A61B 18/00* (2006.01)

(52) U.S. Cl.
CPC ............... *A61B 18/1815* (2013.01); *A61B 2018/00023* (2013.01); *A61B 2018/00577* (2013.01);
(Continued)

(58) Field of Classification Search
CPC ...... A61B 18/1815; A61B 2018/00023; A61B 2018/00577; A61B 2018/00702;
(Continued)

(56) References Cited

U.S. PATENT DOCUMENTS

| | | | | |
|---|---|---|---|---|
| 2010/0152725 | A1* | 6/2010 | Pearson | A61B 18/12 606/41 |
| 2011/0118724 | A1* | 5/2011 | Turner | A61B 18/1815 606/33 |

(Continued)

OTHER PUBLICATIONS

International Search Report and Written Opinion received for PCT Patent Application No. PCT/US2021/012860, mailed on Apr. 30, 2021, 13 pages.

*Primary Examiner* — Khadijeh A Vahdat
*Assistant Examiner* — Abigail M Ziegler
(74) *Attorney, Agent, or Firm* — Pauly, DeVries Smith & Deffner, LLC

(57) ABSTRACT

Various aspects of the present disclosure are directed apparatuses, systems, and methods that may include a microwave ablation system. The microwave ablation system may include a microwave ablation needle, a controller, a microwave generator configured to provide ablation power to the microwave ablation needle, and a pump configured to provide a coolant to the microwave ablation needle at a flow rate, such that the microwave ablation needle emits microwave radiation based on the received ablation power and the controller is configured to perform a plurality of predefined processes having an associated applied ablation power and coolant flow rate.

19 Claims, 11 Drawing Sheets

(52) U.S. Cl.
CPC ............... *A61B 2018/00702* (2013.01); *A61B 2018/00738* (2013.01); *A61B 2018/00744* (2013.01); *A61B 2018/00791* (2013.01); *A61B 2018/1838* (2013.01); *A61B 2018/1846* (2013.01); *A61B 2018/1869* (2013.01)

(58) Field of Classification Search
CPC .. A61B 2018/00791; A61B 2018/1838; A61B 2018/1846; A61B 2018/1869; A61B 2018/00642; A61B 2018/00744
See application file for complete search history.

(56) References Cited

U.S. PATENT DOCUMENTS

| | | |
|---|---|---|
| 2012/0053577 A1 | 3/2012 | Lee et al. |
| 2012/0232549 A1 | 9/2012 | Willyard et al. |
| 2014/0257265 A1* | 9/2014 | Godara ................ A61B 10/025 606/33 |
| 2015/0112190 A1 | 4/2015 | Hancock |
| 2016/0038228 A1* | 2/2016 | Daniel ................ A61B 18/1477 606/40 |
| 2016/0081747 A1 | 3/2016 | Thiel et al. |
| 2019/0321097 A1 | 10/2019 | Cao et al. |
| 2019/0328454 A1* | 10/2019 | van der Weide .. A61B 18/1815 |
| 2019/0357751 A1 | 11/2019 | Friedlander et al. |
| 2020/0046414 A1* | 2/2020 | Brannan ................ A61B 34/25 |
| 2022/0104876 A1* | 4/2022 | Beale ................ A61B 18/1815 |

* cited by examiner

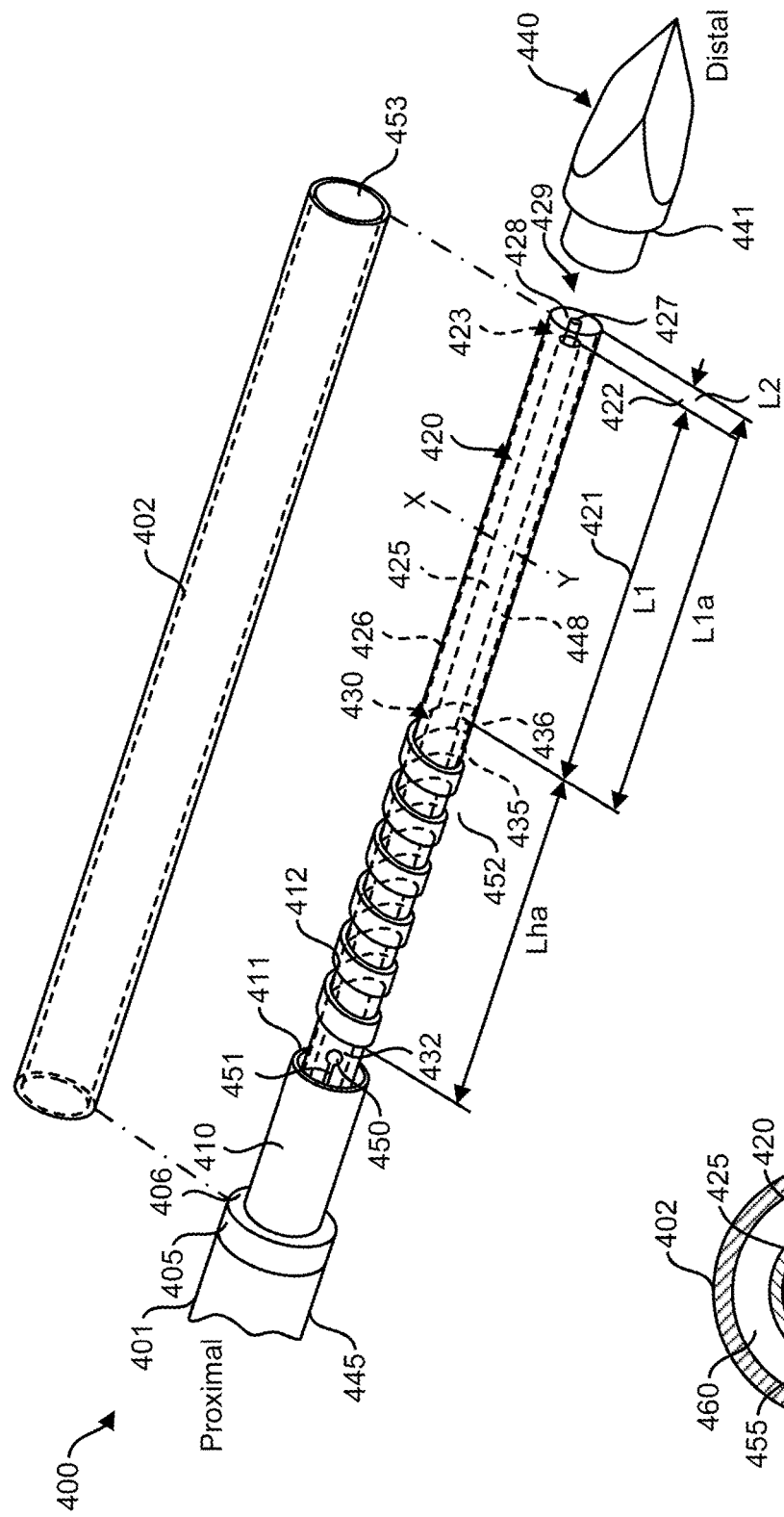
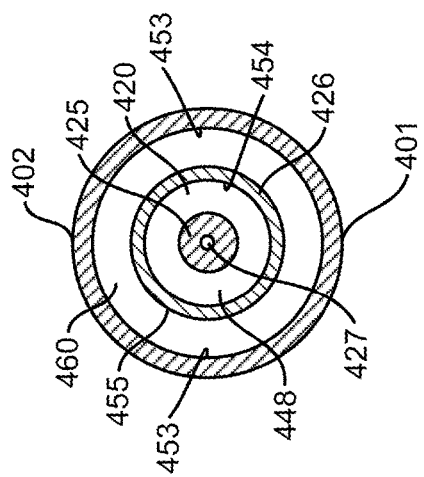
FIG. 4A
FIG. 4B

MICROWAVE ABLATION SYSTEMS AND METHODS HAVING ADJUSTABLE ABLATION PARAMETERS AND MODES OF OPERATION

CROSS REFERENCE TO RELATED APPLICATION

This application claims priority to Provisional Application No. 62/959,573, filed Jan. 10, 2020, which is herein incorporated by reference in its entirety.

FIELD OF INVENTION

The disclosed embodiments generally relate to tissue ablation devices and methods of use.

BACKGROUND OF THE INVENTION

In the treatment of diseases such as cancer, certain types of tissues have been found to denature at elevated temperatures. These types of treatments, known generally as hyperthermia therapies, typically utilize electromagnetic radiation to heat cancerous tissue to temperatures above 60° C. while maintaining healthy tissue at lower temperatures where irreversible cell destruction will not occur. Microwave ablation is one of such treatments utilizing electromagnetic radiation to heat tissue.

Microwave tissue ablation is a less invasive procedure than surgical removal and may be in many situations when tumors are difficult to remove by surgery, for example when the tumor is relatively small, disposed close to a relatively small organ, or disposed close to a major blood vessel. The approach has been used in organs such as the prostate, heart, and liver, where surgical removal of tumors may be difficult to perform.

In order to effectively plan and optimize the procedure, it is desired that the ablation device causes predictably sized and shaped volumes of ablation. For this reason regularly shaped, predictable ablation volumes are preferred, and it is particularly preferred to produce spherical, or near spherical ablation volumes. An ablation device with predictably sized and shaped ablation volumes simplifies the surgical procedures and reduces the undesirable medical complications.

One issue associated with microwave tissue ablation devices relates to possible motion of a microwave ablation device, such as a microwave ablation needle, after placement and during or prior to performing the ablation procedure. For instance, after an ablation needle is placed within a patient so that a desired volume of tissue is to be ablated, the needle may be inadvertently touched, causing the needle to move within the patient and undesirably changing the volume of tissue to be ablated. Additionally or alternatively, the patient may move or be moved, potentially causing the needle to move within the patient and undesirably changing the volume of tissue to be ablated. Depending on the placement of the needle in the patient's tissue, even minor movement, such as due to the patient breathing, may cause the needle to move unintentionally.

Another issue associated with microwave ablation devices relates to the possibility of inserting a device, such as a microwave ablation needle, through cancerous tissue. In some cases, cancer viable cells may be spread through tissue by motion of the needle, known as track seeding. Track seeding can result in cancer cells remaining in tissue even if the primary lesion is successfully ablated via the microwave ablation device.

SUMMARY OF THE INVENTION

In Example 1, a microwave ablation method includes receiving a command to perform a first ablation process; providing coolant to a microwave ablation device at a first flow rate; applying ablation power at a first power level to the microwave ablation device; stopping applying power at the first power level; receiving a command to perform a second ablation process after stopping applying power at the first power level; providing coolant to the microwave ablation device at a second flow rate; and applying ablation power at a second power level to the microwave ablation device, the first ablation process is a stick mode ablation process or track mode ablation process, the second ablation process is a treatment ablation process, and the first flow rate is lower than the second flow rate.

In Example 2, the microwave ablation method of Example 1, the first power level is lower than the second power level.

In Example 3, the microwave ablation method of Example 1, the first power level is the same as the second power level, such that the same amount of ablation power is applied to the microwave ablation device during the second process and the first process.

In Example 4, the microwave ablation method of Example 1, the first power level and the second power level are in the range of 45-90 W.

In Example 5, the microwave ablation method of Example 1, the second flow rate is at least 4 times larger than the first flow rate.

In Example 6, the microwave ablation method of Example 1, the second flow rate is between 95 ml/min and 120 ml/min and the first flow rate is between 10 ml/min and 30 ml/min.

In Example 7, the microwave ablation method of Example 1 further includes stopping applying at the second power level; receiving a command to perform a third process; providing coolant to the microwave ablation device at a third flow rate, the third flow rate being lower than the second flow rate; and applying ablation power to the microwave ablation device at a third power level.

In Example 8, the microwave ablation method of Example 7, the third flow rate is lower than the first flow rate and the third power level is lower than the first power level and the second power level.

In Example 9, the microwave ablation method of Example 7, the third flow rate is greater than the first flow rate, and the third power level is approximately equal to the second power level.

In Example 10, the microwave ablation method of Example 7, the third process includes a track ablation process.

In Example 11, the microwave ablation method of Example 7, the first process includes a stick mode ablation process.

In Example 12, the microwave ablation method of Example 10, performing the track ablation process includes providing instructions, via a user interface, to remove the microwave ablation device from a medium while applying ablation power to the microwave ablation device at the third power level and providing coolant to the microwave ablation device at the third flow rate.

In Example 13, the microwave ablation method of Example 10, providing instructions to remove the microwave ablation device from a medium during or after applying ablation power to the microwave ablation device at the third power level includes providing instructions to remove the device at a predefined rate while providing ablation power to the microwave ablation device at the third power level.

In Example 14, a microwave ablation method includes receiving a command to perform a track mode ablation process; providing coolant to a microwave ablation device at a track mode flow rate; applying ablation power at a track mode power level to the microwave ablation device; and providing instructions for withdrawing the microwave ablation device from a medium.

In Example 15, the microwave ablation method of Example 14, providing instructions to withdraw the microwave ablation device includes providing instructions to withdraw the microwave ablation device from the medium at a prescribed rate.

In Example 16, the microwave ablation method of Example 14 further includes receiving temperature information from a temperature sensor indicative of a temperature near the microwave ablation device; and when the received temperature information satisfies a predetermined condition, stopping applying ablation power to the microwave ablation device.

In Example 17, the microwave ablation method includes receiving a command to perform a stick mode ablation process; providing a coolant to a microwave ablation device at a stick mode flow rate; applying ablation power at a stick mode power level to the microwave ablation device; receiving temperature information representative of a temperature associated with the microwave ablation device; and stopping applying ablation power to the microwave ablation device when either: the temperature information satisfies a predetermined condition, or the ablation power has been applied for a predetermined amount of time.

In Example 18, the microwave ablation method of Example 17 further includes stopping applying ablation power to the microwave ablation device; receiving a command from a user interface to perform a treatment mode process; flowing coolant through the microwave ablation device at a treatment mode flow rate, the treatment mode flow rate being greater than the stick mode flow rate; and applying ablation power to the microwave ablation device at a treatment mode power level.

In Example 19, the microwave ablation method of Example 18, the treatment mode flow rate is at least 4 times larger than the stick mode flow rate.

In Example 20, the microwave ablation method of Example 18, flowing coolant at the treatment mode flow rate creates an ablation zone that is shaped differently from an ablation zone when flowing coolant at the stick mode flow rate.

In Example 21, a microwave ablation system includes a microwave ablation device; a user interface; a controller in communication with the user interface; a microwave generator configured to provide ablation power to the microwave ablation device such that the microwave ablation device emits microwave radiation based on the received ablation power, the ablation power provided to the microwave ablation device being controllable by the controller; and a pump configured to provide a coolant to the microwave ablation device at a flow rate, the flow rate being controllable via the controller, the controller is configured to, upon initiation via the user interface, perform a plurality of predefined processes having an associated applied ablation power and coolant flow rate.

In Example 22, a microwave ablation system according to Example 2, the system further includes a temperature sensor in communication with the controller; and the controller is configured to, upon receiving a command from the user interface, perform a first process including flowing coolant through the microwave ablation device at a first flow rate, applying ablation power to the microwave ablation device at a first power level, and receiving temperature information from the temperature sensor indicative of a temperature within or near the microwave ablation device; cease performing the first process by stopping the application of ablation power to the microwave ablation device if a predetermined amount of time expires or the received temperature information meets a predetermined threshold; and generate a report indicating whether or not the first process was successful; if the received temperature information met the predetermined threshold prior to the predetermined amount of time expiring, the first process is considered successful, and if the predetermined amount of time expired prior to the received temperature information meeting the predetermined threshold, the first process is considered unsuccessful.

In Example 23, a microwave ablation system according to Example 21 or 22, the controller is further configured to, after ceasing performing the first process and upon receiving a command from the user interface, perform a second process including flowing coolant through the microwave ablation device at a second flow rate, the second flow rate being greater than the first flow rate, and applying ablation power to the microwave ablation device at a second power level.

In Example 24, a microwave ablation system according to any preceding Example, the second power level is the same as the first power level, such that the same amount of ablation power is applied to the device during the second process and the first process.

In Example 25, a microwave ablation system according to any preceding Example, the first power level and the second power level are in the range of 45-90 W.

In Example 26, a microwave ablation system according to any preceding Example, the second flow rate is at least 4 times larger than the first flow rate.

In Example 27, a microwave ablation system according to any preceding Example, the second flow rate is between 95 ml/min and 120 ml/min and the first flow rate is between 10 ml/min and 30 ml/min.

In Example 28, a microwave ablation system according to any preceding Example, the controller is further configured to cease performing the second process by stopping application of ablation power to the microwave ablation device, and upon receiving a command from the user interface, perform a third process including flowing coolant through the microwave ablation device at a third flow rate, the third flow rate being lower than the second flow rate, and applying ablation power to the microwave ablation device at a third power level.

In Example 29, a microwave ablation system according to any preceding Example, the third flow rate is lower than the first flow rate and the third power level is lower than the first power level and the second power level.

In Example 30, a microwave ablation system according to any preceding Example, the third process includes a track ablation process.

In Example 31, a microwave ablation system according to any preceding Example, the third flow rate is greater than the first flow rate, and the third power level is approximately equal to the second power level.

In Example 32, microwave ablation system according to any preceding Example, the third process includes a track ablation process, and performing the track ablation process includes providing instructions, via the user interface, to remove the microwave ablation device from a medium while applying ablation power to the microwave ablation device at the third power level and providing coolant to the microwave ablation device at the third flow rate.

In Example 33, a microwave ablation system according to any preceding Example, providing instructions to remove the microwave ablation device from a medium during or after applying ablation power to the microwave ablation device at the third power level includes providing instructions to remove the device at a predefined rate while providing ablation power to the microwave ablation device at the third power level.

In Example 34, a microwave ablation system according to any preceding Example, the second process includes a treatment ablation process.

In Example 35, a microwave ablation system according to any preceding Example, the first process includes a stick mode ablation process.

While multiple embodiments are disclosed, still other embodiments will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

Advantages of the disclosed embodiments may become apparent to those skilled in the art with the benefit of the following detailed description and upon reference to the accompanying drawings.

FIG. 4A is a perspective view of a microwave tissue ablation device 400 according to one embodiment of the disclosure.

FIG. 4B is a sectional view across the line X-Y to illustrate one embodiment of the cooling features.

Figure 1A:
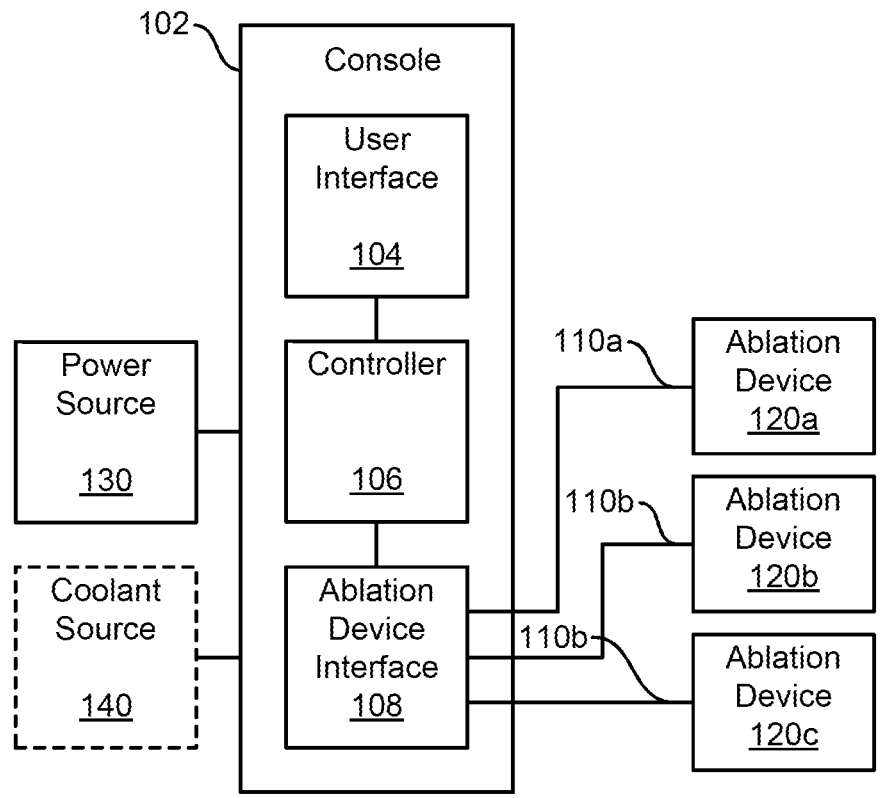
FIG. 1A shows a block diagram including components of a system for performing an ablation process according to one embodiment of the disclosure.

While the invention is susceptible to various modifications and alternative forms, specific embodiments thereof are shown by way of example in the drawings. The drawings may not be to scale.

DETAILED DESCRIPTION OF THE INVENTION

The size and dimension of an ablation area created by the microwave tissue ablation device is dependent, among other factors, on the type of microwave antenna. Clinicians may select a microwave antenna capable of generating an ablation region greater than the size and dimension of the target tissue and insert the microwave antenna such that the ablation region created by the microwave antenna includes the target tissue. Where the tissue to be ablated is larger than the size of the ablation volume produced by the device, more than one device may be used and the ablation volumes combined to cover the tissue to be ablated. The embodiments of the microwave tissue ablation device described herein may be used to create predictably shaped ablation regions, with reduced tailing which aids ablation planning and prevents damage to tissue outside the volume to be treated.

In some embodiments, ablation devices disclosed herein are microwave ablation devices configured to cause ablation by emission of microwave energy, which kills the tissue by heating. Typically the devices are microwave ablation needles having microwave antennas such as those described herein.

In a further aspect, the invention provides a system for microwave ablation of tissue comprising one or more microwave ablation devices such as probes or needles as described herein, the microwave ablation device comprising a microwave antenna configured to transmit microwave energy to tissue, a microwave generator configured to provide microwave energy to the microwave antenna via a feedline, one or more power cables configured to connect the microwave generator to the microwave antenna of the ablation devices and to deliver microwave energy provided by the microwave generator to the antenna for the ablation of tissue.

Ablation devices such as those described herein can be configured to operate at powers of up to 150 watts and for periods of up to 20 minutes or more. The devices heat up during use due to resistive heating of the antenna and to energy reflected from the tissue and therefore typically at least the distal portion of the device including a distal portion of the feedline and the antenna will require cooling. Conveniently, in various embodiments, the whole feedline and antenna are cooled. Cooling the antenna prevents the device itself becoming damaged and prevents tissue close to the antenna becoming over heated or charred. This alters the physical properties of the tissue, including its energy absorption and reflection characteristics and therefore reduces the efficiency of the antenna and may alter the ablation zone. In an embodiment the tissue ablation devices above therefore may additionally comprise a cooling system to cool the antenna and/or at least a portion of the feed line. Such cooling systems are typically configured to pass a cooling fluid such as a coolant (e.g. water) over at least a portion of the feedline and over the antenna. Typically such systems comprise a coolant inlet and a coolant outlet which co-operate to pass a coolant over the antenna and optionally at least a portion of the feedline to cool the antenna and optionally at least a portion, optionally all, of the feedline. The antenna and feedline are typically in contact with the coolant.

In one option the cooling system comprises a coolant chamber surrounding the antenna and at least a distal portion of the feedline and having a coolant inlet conduit, configured to supply coolant to the coolant chamber and a coolant outlet conduit configured to carry coolant away from the coolant chamber, the coolant inlet and coolant outlet conduits configured to pass coolant over at least a portion of the feedline and at least a portion of the antenna.

FIG. 1A shows a block diagram including components of a system for performing an ablation process according to one embodiment of the disclosure. The system includes a console 102 including a user interface 104, controller 106, and an ablation device interface 108. In an embodiment, user interface 104 includes a display for presenting information to a user and an input device for receiving inputs from the user, such as via one or more buttons, dials, switches, or other actuatable elements. In an embodiment, user interface 104 comprises a touchscreen display that functions as both the display and the input device of the user interface 104.

According to an aspect of the invention, the ablation device interface 108 of the console 102 is arranged to interface with one or more ablation devices. In the embodiment of FIG. 1A, ablation device interface 108 interfaces with three ablation devices 120a, 120b, 120c via lines 110a, 110b, 110c, respectively. In an embodiment, a console 102 can interface one, two, or all three ablation devices (120a, 120b, 120c) individually or simultaneously. It will be appreciated that, while three ablation devices are shown in the embodiment of FIG. 1A, different aspects of the invention may include a console having an ablation device interface capable of interfacing with different numbers of ablation devices.

In an embodiment, a console includes an ablation device interface capable of interfacing with a single ablation device. In other embodiments, a console includes an ablation device interface capable of interfacing with two ablation devices, with three ablation devices, with four ablation devices, or with five ablation devices. In some examples, an ablation device interface can be configured to interface with any number of ablation devices.

According to certain aspects of the invention, a console can be used to operate any number of ablation devices up to the number of ablation devices supported by the ablation device interface. For example, a console having an ablation device interface capable of receiving three ablation devices simultaneously can be configured to operate one, two, or three ablation devices.

In an embodiment, lines 110a, 110b, 110c are configured to provide a coolant (e.g., from a coolant source 140) and ablation power (e.g., microwave signals) to ablation devices 120a, 120b, 120c, respectively. Lines 110a, 110b, 110c can be configured to provide a path for a coolant to be provided to a respective ablation device and a return path for receiving coolant from the respective ablation device after having traversed a coolant flow path within the ablation device.

According to an aspect of the invention, the controller 106 is configured to interface with the user interface 104 and the ablation device interface 108. In an embodiment, the controller 106 can be configured to receive one or more inputs via the user interface 104 and output one or more items via the user interface 104.

The controller 106 can be configured to control operation of one or more ablation devices (e.g., 120a, 120b, 120c) via the ablation device interface 108. In an embodiment, controller 106 can cause coolant to be provided to one or more ablation devices via the ablation device interface 108. The controller 106 can cause ablation power to be provided to one or more ablation devices in order to cause the ablation device to perform an ablation process. In an embodiment, the ablation power provided to an ablation device causes a microwave ablation device to emit microwave radiation. A power source 130 can provide electrical power used to generate the ablation power.

In an example, the controller includes one or more processors and memory comprising instructions for causing the one or more processors to be performed via the controller. In various embodiments of the invention, a controller may be implemented as one or more processors, such as one or more microprocessors, digital signal processors (DSPs), application specific integrated circuits (ASICs), field programmable gate arrays (FPGAs), programmable logic circuitry, or the like, either alone or in any suitable combination. A controller may also include memory that stores program instructions and related data that, when executed cause the controller to perform the functions attributed thereto in this disclosure. Memory may include any fixed or removable magnetic, optical, or electrical media, such as RAM, ROM, CD-ROM, flash memory, EEPROM, or the like. Memory may also include a removable memory portion that may be used to provide memory updates or increases in memory capacities. A removable memory may also allow image data to be easily transferred to another computing device. A controller may also be implemented as a System on Chip that integrates some or all components of a computer or other electronic system into a single chip.

Figure 1B:
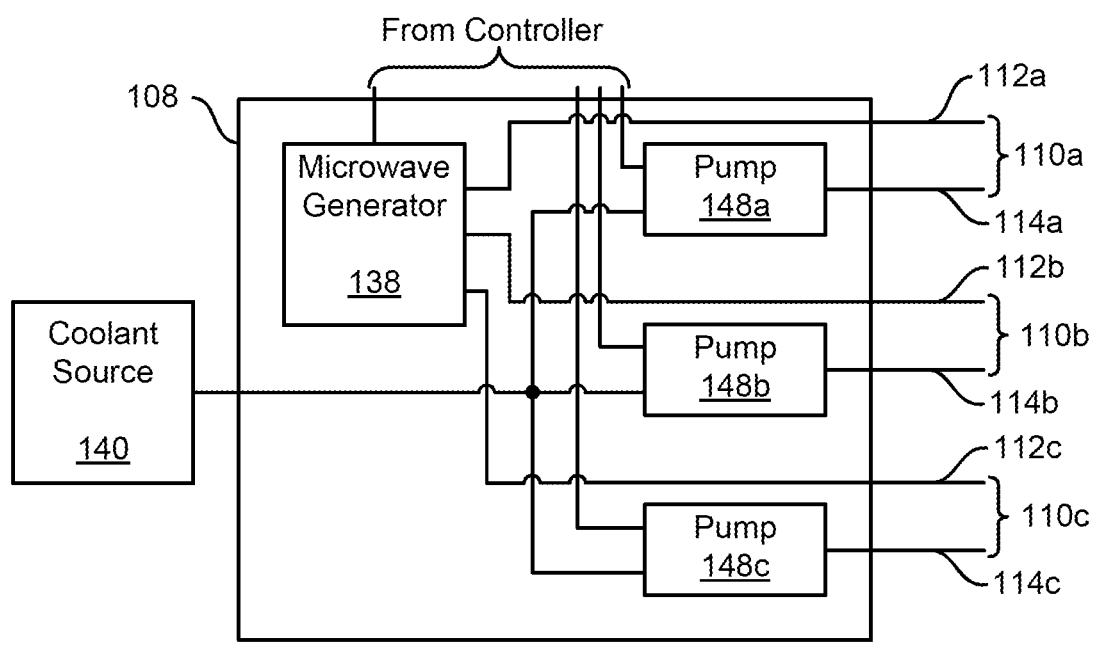
FIG. 1B shows a block diagram demonstrating operation of an ablation device interface for interfacing with an ablation device for performing an ablation process according to one embodiment of the disclosure.

FIG. 1B shows a block diagram demonstrating operation of an ablation device interface for interfacing with an ablation device for performing an ablation process according to one embodiment of the disclosure. In an example, an ablation device interface 108 includes one or more fluid pumps, each of the one or more fluid pumps (148a, 148b, 148c) being configured to pump a coolant to a respective ablation device. For example, as shown, pump 148a is in communication with coolant source 140, and can be configured to provide coolant to an ablation device (e.g., 120a) via a coolant line 114a. Such pump(s) can be controlled by the controller. The controller can be configured to control the flow rate of fluid provided from a pump (e.g., 148a) to an ablation device (e.g., 120a), including initiating the pump providing the coolant to the ablation device and stopping the pump providing the coolant to the ablation device.

In the example of FIG. 1B, the ablation device interface 108 includes three pumps 148a, 148b, 148c for providing coolant to a respective ablation device via coolant lines 114a, 114b, 114c, respectively. Coolant lines 114a, 114b, 114c can be included in lines 110a, 110b, 110c shown in FIGS. 1A and 1B, respectively. In an embodiment, each pump is controlled by the controller and independently from the other pumps, for example, whereby any pump can operate independently of the operating status of the other pumps.

In another embodiment, each of pumps 148a, 148b, 148c comprises a peristaltic pump driven by a single motor controlled by the controller. In some such examples, each pump operates at the same rate defined by the motor, and coolant flows through any connected ablation devices via coolant lines 114a, 114b, 114c. The controller can adjust the flow rate of coolant through the ablation devices by controlling the speed of the motor.

In some examples, coolant provided to the ablation device is provided in a closed loop recirculation system, wherein coolant is received from the ablation device and returned to the coolant source 140. In an embodiment, coolant source 140 comprises a reservoir of coolant, such as sterile water, from which coolant is drawn, directed to one or more ablation devices via a coolant line, and returned to the reservoir from the one or more ablation devices via a coolant outlet line configured to carry coolant away from the ablation device. In some alternate examples, coolant outlet line(s) carry coolant away from the ablation device toward a waste system (e.g., toward a drain).

The ablation device interface of FIG. 1B includes a microwave generator 138 for generating and providing microwave signals to a microwave antenna in a microwave ablation device configured to transmit microwave energy to tissue. Providing microwave signals to the ablation device can include providing ablation power to the ablation device such that the device emits microwave radiation. Microwave generator 138 can provide microwave signals to ablation devices via power cable. In the embodiment of FIG. 1B, microwave generator 138 can provide microwave signals to up to three ablation devices via power cables 112a, 112b, 112c, respectively.

Power cables 112a, 112b, 112c may be coaxial cables which are may be rated to at least 30 watts, optionally at least 100 watts, and further may be at least 150 watts power. The cables may be cooled cables configured to be cooled by a coolant supply, such as by circulating coolant along the cable between a cable coolant inlet and a cable coolant outlet. In some examples, coolant lines 114a-c provide coolant along power cables 112a-c, respectively. In an example configuration, the system comprises a cooling system and the cooling system is configured to cool both the cable and the microwave ablation device.

In some examples, the microwave generator may be configured to supply microwave energy to the antenna in one or more of the 915 MHz range, the 2.45 GHz range, or the 5.8 GHz range, optionally in the 2.45 GHz range, and further may be at or about 2.45 GHz. The microwave generator may be configured to provide microwave energy to the antennas of up to 5 microwave ablation probes, for example, one, two, or three probes.

The microwave generator 138 can be configured to provide microwave signals prescribed by the controller 106. For example, in an example embodiment, the controller 106 can instruct the microwave generator 138 to provide particular microwave signals to a particular ablation device. The controller can be configured to designate a particular ablation magnitude (e.g., desired microwave power and/or energy emitted from ablation device, etc.), ablation duration, or other parameters, such as a duty cycle, phase shift, or other parameters associated with the microwave signal. In some examples, the microwave signal includes an electrical power (e.g., 45-90 W) delivered at the ablation needle. The microwave signal can include an electrical signal including properties (e.g., electrical power, frequency, etc.) in order to cause the ablation device to emit microwave radiation having desired characteristics (e.g., microwave power radiated to surrounding tissue, etc.). The electrical signal can provide a desired ablation power to the microwave ablation device.

In an embodiment, the controller 106 can instruct the microwave generator 138 to apply microwave signals to each of a plurality of ablation devices. For example, with respect to FIG. 1B, the controller can instruct the microwave generator 138 to provide a first microwave signal to a first ablation device via power cable 112a, provide a second microwave signal to a second ablation device via power cable 112b, and provide a third microwave signal to a third ablation device via power cable 112c. In some such examples, the microwave generator 138 can provide such first, second, and third microwave signals simultaneously. Such signals can be the same signal or different signals. For example, in an embodiment, the same level of ablation power is provided by each of the first, second, and third microwave signals.

In some examples, the controller may be configured to control one or more of the following parameters: the output wavelength, the output power, the time period over which microwave energy is delivered to one or more of the antennas, the time period over which energy is delivered at an output power. Where the ablation device comprises a sensor, such as a temperature sensor, the controller can be configured to control any one or more of the parameters in response to a signal from the sensor (e.g., a temperature measurement). For example the controller may be configured to switch off the power to one or more of the antennas in response to an over temperature condition.

While shown in FIG. 1B as being implemented as a single microwave generator 138 configured to provide microwave signals to a plurality of ablation devices, in some examples, an ablation device interface 108 can include a plurality of microwave generators, each corresponding to a respective ablation device. In an embodiment, the controller 106 is in communication with a plurality of microwave generators and can be configured to cause the plurality of microwave generators to apply microwave signals to respective power cables (e.g., 112a, 112b, 112c) to provide such microwave signals to respective ablation devices.

FIG. 1B shows an example embodiment wherein three lines 110a, 110b, 110c can provide microwave signals and coolant to a respective three ablation devices simultaneously. In some aspects of the invention, microwave signals and coolant can be provided to a subset of lines 110a, 110b, 110c, for example, if fewer than three ablation devices are connected to the console 102. Further, in some aspects, microwave signals and coolant can be provided to a subset of lines 110a, 110b, 110c even if three ablation devices are connected to the console 102. For example, one or more such connected ablation devices can remain unused.

In an embodiment, controller 106 controls which ablation devices (e.g., which lines of 110a, 110b, 110c) receive microwave signals and coolant. In an aspect of the invention, the controller 106 can control aspects of the microwave signal, such as magnitude, frequency, duty cycle, duration, etc. of the microwave signal. In another aspect of the invention, the controller 106 can control aspects of providing the coolant to an ablation device, such as controlling a flow rate of the coolant, for example, by controlling operation of a respective pump. In an embodiment, for each ablation device, the controller controls aspects of both the microwave signal applied to an ablation device and aspects of providing the coolant to the ablation device. During operation, different ablation devices can each receive microwave signals and amounts of coolant independent of the signals and fluid received at other ablation devices, and can be the same as or different from microwave signals and amounts of fluid provided to other ablation devices.

While FIG. 1B shows an ablation device interface for interfacing with three ablation devices, it will be appreciated that a console according to different embodiments can include an ablation device interface capable of interfacing with a different number of ablation devices.

It will be appreciated that, while the block diagram of FIG. 1B shows an ablation device interface 108 including several components for interfacing with ablation devices, the components shown as being a part of the ablation device interface 108 are not necessarily contained within a single module or housing. Such components are grouped into the ablation device interface in that such components facilitate control of connected ablation devices by controller 106.

Additionally, while FIG. 1B shows an ablation device interface for interfacing with microwave ablation devices, it will be appreciated that similar ablation device interface concepts can be used to provide an interface between a controller and other ablation devices, such as RF ablation, cryoablation, or the like.

In an embodiment, the ablation device interface includes one or more ports configured to receive a portion of an ablation device, such as a cartridge having a fluid interface for connecting to a fluid line (e.g., 114a) and an electrical interface for connecting to a power cable (e.g., 112a). Example cartridges and corresponding ablation device interface configurations are described in U.S. Patent Application No. 62/884,044, filed on Aug. 7, 2019 and entitled "Cooling System for Surgical Device, which is incorporated by reference in its entirety.

Figure 2:
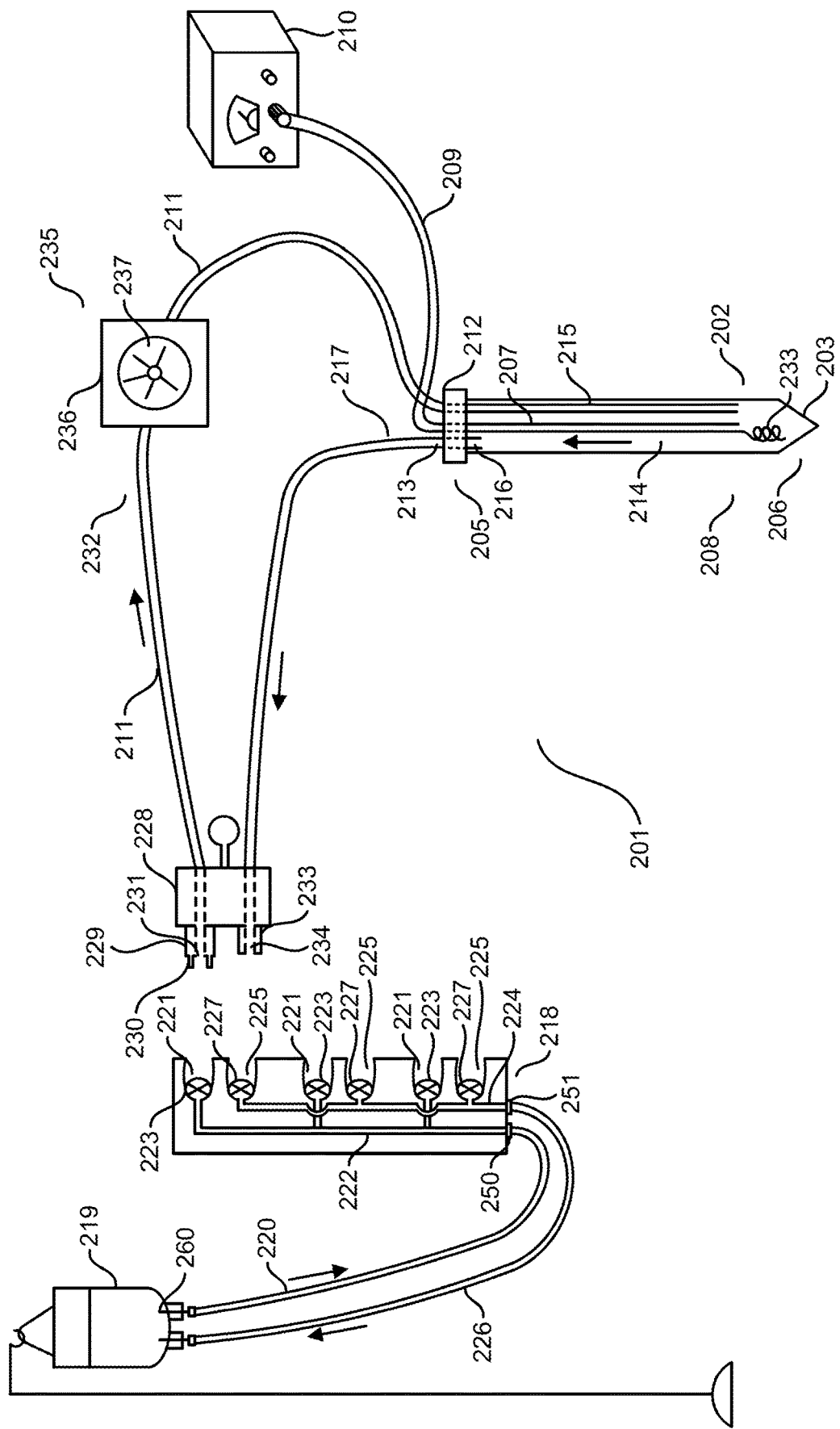
FIG. 2 is a simplified illustration of a cooling system according to the disclosure.

FIG. 2 is a simplified illustration of a cooling system according to the disclosure. The system 201 comprises an ablation device 202, in this case the microwave ablation device comprises a microwave ablation needle which is configured to deliver microwave energy to a patient's tissue to ablate the tissue. The cooling system may also be used in relation to other cooled ablation devices such as radiofrequency (RF) ablation devices for example.

The microwave ablation device 202 may have a tip 203 configured to penetrate tissue and an elongated shaft having a proximal end 205 and a distal end 206. The shaft encloses a coolant chamber 214 and a feedline 207, which may be a coaxial cable having an inner conductor, an outer conductor, and a dielectric therebetween (not shown in FIG. 2). The feedline of FIG. 2 comprises, distally, a radiating region 208 comprising a microwave antenna 233. The proximal end of the feedline 207 may be attached to a cable 209 (typically a coaxial cable) connecting the microwave ablation device 202 to a microwave generator 210 for providing microwave energy to the device. The cable may be releasably connectable, or, as in this case, permanently attached to the device. In some embodiments, as shown with respect to FIGS. 1A and 1B, the microwave generator 210 may be housed within a console, such as console 102.

The device is provided with coolant via a device coolant supply line 211 which may be permanently attached to the device coolant inlet 212. In some embodiments, the device coolant supply line may, alternatively, be releasably connectable to the coolant inlet 212 such as via a Luer® type connector. The device coolant inlet 212 is in fluid communication with the device coolant outlet 213, via a series of coolant passageways 214, 215, and 216 configured to circulate coolant within the device. In this simplified representation, coolant enters the device through the coolant inlet tube 215, circulates through a coolant chamber 214 to cool the device, and leaves via the coolant outlet tube 216 and device coolant return line 217.

System 201 is provided with a manifold 218 which receives coolant fluid from a coolant fluid supply 219, via a coolant system supply line 220. The coolant system supply line 220 may be permanently connected to the manifold 218 at the manifold fluid supply inlet 250 or it may be releasably connectable to the manifold fluid supply inlet 250, for example by a LuerLok® connector. The coolant fluid supply may be, for example, an IV bag. The in-flowing coolant may be distributed to one or more manifold outlet ports 221, via a manifold inflow conduit 222. In an advantageous embodiment, and as illustrated in FIG. 2, flow of coolant out of the manifold outlet port 221 may be controlled by a manifold outlet valve 223. This valve may be normally in the closed position. In some embodiments, as shown with respect to FIGS. 1A and 1B, the manifold 218 may be housed within a console, such as console 102.

The manifold 218 also comprises a manifold coolant outflow conduit 224 which provides a fluid connection between one or more manifold fluid inlet ports 225 and the coolant system return line 226. The coolant system return line 226 may be permanently connected to the manifold 218 at the manifold fluid return inlet 251 or it may be releasably connectable to the manifold fluid supply inlet 250, for example by a LuerLok® connector. In an optional embodiment, a manifold inlet valve 227 controls the flow through each inlet port and may also normally be in the closed state.

A supply coupling 229 is configured for connection to a manifold outlet port 221. The system may also comprise a return coupling 233 which is configured for connection to a manifold inlet port. In an optional embodiment, the manifold outlet valve 223 may be configured to open upon connection of the supply coupling 229. In one approach, the supply coupling may comprise projections 230 which cause the valve to open upon connection of the coupling 229, to the manifold outlet port 221, but other arrangements are possible as discussed elsewhere herein.

A coolant circuit coolant inlet 231 on the supply coupling 229 is in fluid communication with the device coolant supply line 211 so that connection of the supply coupling 229 to the manifold outlet port 221 places the cooling circuit 232 in fluid communication with the cooling fluid supply 219.

A return coupling 233 may have a coolant circuit outlet 234 in fluid communication with the device coolant return line 217. The supply coupling 229 and the return coupling 233 can be arranged for simultaneous connection to the manifold outlet port 221 and manifold fluid inlet port 225 respectively.

A pumping portion 235 may be arranged in the device cooling circuit 232 and may be arranged in the supply line 211 for example, and is arranged to circulate the coolant through the microwave ablation device 202. In the system shown in FIG. 2, the pump is a disposable pump head 236 having pump vanes 237, permanently connected in the device coolant supply line 211 and adapted to be connected to a pump head drive (not shown). Alternative pumping portions may be used and are described elsewhere herein. In some embodiments, as shown with respect to FIGS. 1A and 1B, the pumping portion 235 may be housed within a console, such as console 102.

Figure 3:
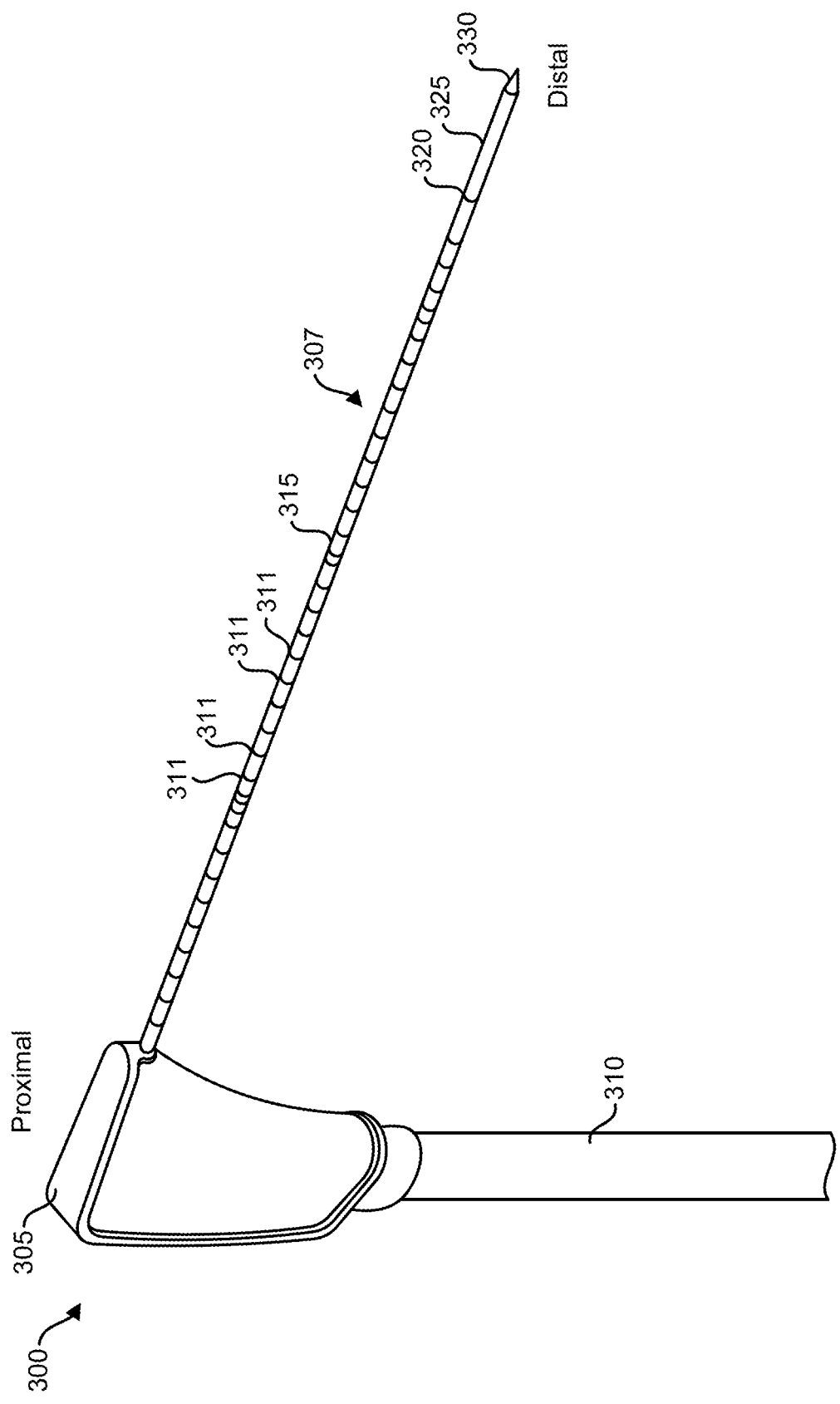
FIG. 3 is a perspective view of a microwave tissue ablation device with a handle according to one embodiment of the disclosure.

FIG. 3 is a perspective view of a microwave tissue ablation device 300 with a handle 305 according to one embodiment of the disclosure.

The microwave tissue ablation device 300 includes a handle 305. The handle 305 is configured to provide a firmer grip for a surgeon to handle the microwave tissue ablation device 300. The handle 305 is further configured to house liquid manifolds for coolant circulation and coaxial connectors for powering the feedline.

The microwave tissue ablation device 300 includes a probe 307. The probe 307 is configured to be inserted into patient's body for heating target tissue. In one embodiment, the probe 307 includes various ablation device components described elsewhere herein, such as the feedline, asymmetric dipole antenna, cooling system having inflow tubes and outflow tubes, etc. In an embodiment, the microwave antenna is configured to emit microwave radiation in a frequency band selected from the 915 MHz band (902 to 928 MHz), the 2.45 GHz band (2.402 to 2.483 GHz), and/or the 5.8 GHz band (5.725 to 5.875 GHZ). The wavelength may be within the 2.45 GHz band and particularly the antenna may be configured to emit microwave energy at or about 2.45 GHz. The devices are configured to operate at up to 150 watts power supplied to the antenna.

The probe 307 includes a surface 315. The surface 315 is configured to be in contact with human tissue and is made with biocompatible materials. The device shaft is at least partially, metal, e.g., stainless steel and includes markings 311, e.g., laser markings. The markings 311 are configured to inform the surgeon of the depth of the probe penetration into the body. It may comprise a lubricious surface layer such as PTFE, to aid insertion and prevent tissue sticking to the needle shaft while the needle is being inserted or extracted.

The shaft of devices herein is typically cylindrical and is typically made of a biocompatible polymer, a biocompatible composite material, such as glass fiber reinforced polymer or carbon fiber reinforced polymer, ceramic or metal (such as stainless steel). The shaft may be made of ceramic or metal, but in an optional embodiment the shaft comprises metallic portion and a non-metallic portion. The non-metallic portion may be a biocompatible composite material, such as glass fiber reinforced polymer or carbon fiber reinforced polymer or ceramic. Optionally, the non-metallic portion may be ceramic due to its improved performance and strength. The ceramic may be an alumina or zirconia ceramic.

The shaft of the devices can terminate distally in a device cap. The shaft is sometimes cylindrical. The feedline and antenna may be disposed within the device shaft. The device shaft typically extends from a proximal manifold and terminates distally in a distal cap. The manifold comprises electrical connections to electrical components of the shaft such as the feedline, and may also comprise coolant inlet and outlet connections, where necessary.

The diameter of the shaft is not limited, and is typically adapted for the intended purpose, for example for ablation needles, it is important to have a narrow needle to limit damage caused at insertion and to provide fine control of positioning, consequently the needle shaft is between 1.4 mm and 3 mm in diameter, such as between 1.5 mm and 2.5 mm, and more particularly 2 mm to 2.5 mm.

The devices herein as illustrated by probe 307 of FIG. 3 may include an applicator cap 330. In an embodiment, applicator cap 330 is made of a biocompatible metal or a ceramic, e.g., stainless steel or a ceramic. The applicator cap 330 can include a circular base and a distal tip (e.g., a trocar tip). The applicator cap 330 tip can include a sharp end disposed at a distal end of the applicator cap 330 and configured for penetration of tissue. The circular base can be configured to be sealed with a sheath of the probe 307 such that the interior of the probe 307 is fluidly isolated from the exterior of the probe 307.

The shaft of devices herein may further comprise an echogenic region on the outer surface configured to be visible under ultrasound, imaging. In one embodiment, this region comprises a coating comprising acoustically-reflective microspheres. The echogenic region extends at least to cover the region of the shaft radially outward of the antenna. The probe 307 of FIG. 3 includes an echogenic region 325 configured to be visible under ultrasound, imaging and one embodiment, comprises a coating comprising acoustically-reflective microspheres.

Where the shaft of devices of the invention comprise a metallic portion and a non-metallic portion, the joint between the two portions, where the metallic portion and the non-metallic portion abut, may be a point of potential weakness, especially where the non-metallic portion is ceramic, since ceramic is typically less flexible and more brittle than metals such as stainless steel. The shaft may additionally comprise a resilient element between this portion and the metallic portion configured to provide resilience to the joint between the non-metallic (e.g., ceramic) portion and the metallic portion of the probe shaft in use.

The devices, (with reference to probe 307) may further include a region 320 configured to relieve strain on the probe induced during use, such as that caused by flexing of the shaft. This strain relief region 320 is particularly useful when the distal portion of the probe sheath is ceramic. The strain relief region 320 is configured to provide the probe 307 added resilience to the joint avoiding fracture of the probe 307 during a medical operation.

Although a resilient element may also be present between a non-metallic region and the cap, it is not necessary since the strains on the shaft at this point are lower. The strain relief region may, for example, comprise a resilient annular spacer, which may be made of a resilient thermoplastic elastomer, such as polyether block amide (PEBA)-tradename PEBAX® or Vestimid®E (Evonik Industries) or a polyaryletherketone (PAEK) such as Polyether ether ketone (PEEK). The spacer may be shaped and configured to space apart the proximal end of the non-metallic portion from the distal end of the metallic portion. The resilient spacer can abut the metallic portion on a proximal face and the non-metallic portion on a distal face. The resilient annular spacer typically extends radially outward to form a surface flush with the outer surface of the probe shaft. The radially inner portion of the annular spacer may be extended proximally and/or distally to provide an annular step configured to support the inner face of the proximal end of the non-metallic portion and/or the distal end of the metallic portion. In an optional embodiment, the annular spacer is extended proximally to provide an annular step configured to support the inner face of the distal end of the metallic portion, but does not extend distally. The device shafts may also comprise an adaptor sleeve to support the joint between the non-metallic portion and the metallic portion of the shaft. The adaptor may be configured to take account of any differences in thickness between the non-metallic portion and metallic portion of the shaft, such as to provide a smooth surface transition between the metallic and non-metallic portions. It may be metallic, or non-metallic such as a thermoplastic elastomer, such as a PEBA PEBAX® or Vestimid®E or a PAEK such as PEEK. The adaptor is particularly important where the non-metallic portion is ceramic due to the thickness required for additional strength of the ceramic and the danger of flexing of the shaft causing cracking at this point. Conveniently the sleeve extends each side of the joint sufficiently to provide support for the joint and is typically positioned radially inward of the shaft, typically between the feedline and the inner wall of the shaft. The adapter sleeve may be metallic.

The resilient spacer and the adaptor sleeve (where present) together comprise a strain relief region. The resilient spacer and the adaptor sleeve may be a single piece or separate, where they are a single piece they can be non-metallic and further may be of a thermoplastic elastomer as described above.

In an optional embodiment, the strain relief region comprises a resilient spacer as described above, shaped and configured to space apart the proximal end of the non-metallic portion from the distal end of the metallic portion, the spacer configured to abut the metallic portion on a proximal face and the non-metallic portion on a distal face, the spacer extending radially outward to form a surface flush with the outer surface of the probe shaft, the radially innermost portion of the spacer extending proximally to provide an annular step configured to support the inner face of the distal end of the metallic portion of the shaft; the strain relief region additionally comprising an adaptor sleeve, which may be metallic, extending each side of the joint and radially inward of the annular spacer. The sleeve may extend proximally of the annular spacer and is configured to be in contact with and support the inner face of the distal end of the metallic portion of the shaft; and may extend distally of the spacer and is configured to be in contact with and support the inner face of the proximal end of the ceramic portion of the shaft.

The microwave tissue ablation device illustrated 300 includes a housing 310. The housing 310 houses coaxial cables, fluid lines, electric lines, etc.

FIGS. 4A and 4B are illustrative of several features of the device. FIG. 4A is a perspective view of a microwave tissue ablation device 400 according to one embodiment of the disclosure. FIG. 4B is a sectional view across the line X-Y to illustrate one embodiment of the cooling features.

The microwave tissue ablation device 400 of FIG. 4A has a shaft 401 surrounding and typically coaxial with both the microwave antenna and at least a portion of the feedline. The shaft typically extends from a proximal manifold to a distal cap. Both the antenna and the feedline are disposed within the shaft. The shaft may be of unitary construction or it may have a metal portion 445 and a non-metallic portion such as a ceramic portion 402 as shown in the figure. Where present, the non-metallic portion may extent axially to be at least co-extensive with the antenna. In FIG. 4A, the ceramic portion extends from distal end 406 of a collar 405 to the base 441 of the cap 440. The ceramic portion 402 is shown separately from the shaft 401 in order to show the internal features of the device.

As illustrated, the microwave tissue ablation device 400 may include a resilient element (e.g. collar 405), and an adaptor 410 to join the metal portion 445 to the ceramic portion 402 of the shaft. In devices of the invention, an adaptor may be used to take up any difference in shaft thickness between the two portions and additionally may act to reduce flexing between the metal portion 445 and the ceramic portion 402. In devices of the invention, a resilient annular spacer between the ceramic portion and the metal portion of the shaft, as shown here, acts to provide resilience to this region and so reduces the occurrence of fractures at this point due to strain on the shaft during use.

As described, for example, with respect to FIGS. 1A and 1B, microwave energy generated by a microwave generator can be supplied to the antenna 452 by a power cable which electrically connects the microwave generator to the feedline 432 of the antenna 452 within the microwave tissue ablation device 400. The microwave ablation devices also have a shaft surrounding and typically co-axial with both the microwave antenna and at least a distal portion of the feedline. The shaft typically extends from a proximal manifold to a distal cap.

The feedline may comprise an inner conductor, an outer conductor and a dielectric disposed there-between. The feedline may comprise a further dielectric or insulator which insulates the outer conductor from other parts of the device and acts as an outer insulator to the feedline, but it is not required in all embodiments. In some embodiments the further dielectric may be absent from the distal portion of the feedline, at least up to the junction point. The feedline may lack such a further dielectric within the device shaft, such as between a proximal feedline connector of a distal manifold, and the junction point of the antenna. The feedline is typically a co-axial cable having a central conductor, surrounded by a first dielectric, or insulator, the first dielectric being surrounded by the second conductor, which may be covered by the further dielectric or insulator as described above. The inner conductor is typically the power conductor.

Referring to FIG. 4A, microwave tissue ablation device 400 has an antenna 452 including a helical arm 412, and a linear arm 420. A distal end 435 of the helical arm 412 forms an electrical connection with the outer conductor 430 of the feedline 432 at a junction point 436 and extends distally from the junction point 436. The helical arm 412 forms no other electrical contact with the inner conductor 427 or the outer conductor 430, except at the junction point 436.

The junction point 436 is conveniently towards, or at, the distal most end of the feedline 432. The feedline 432 may extend beyond the junction point 436 in order to provide suitable mechanical support to the electrical junction, as described elsewhere herein. It may not extend by more than 2 mm and particularly not more than 1 mm beyond the junction point 436. Typically the helical arm is in the form of a single conductor. The helical arm of the antenna may be in the form of a wire or a ribbon, but is typically a wire having a circular cross section or a ribbon. The helical arm may be in the form of a cylindrical conductor, having a helical gap running from its proximal to its distal end to give a helical conductor having a planar conductor surface curved about the feedline and/or the linear arm. The helical arm does not make any other contact with either the inner conductor or the outer conductor, except at the junction point.

In the example of FIG. 4A, the helical arm 412 extends proximally from the junction point 436 in a series of turns about the feedline 432 and so is coaxially disposed about the feedline 432. The helical arm 412 forms no other electrical contact with the inner conductor 427 or the outer conductor 430, except the junction point 436. The helical arm may be affixed to a substrate as described elsewhere herein, such as by an adhesive in order to hold it in place and to make assembly easier. The helical arm may be embedded within a matrix such as a polymer layer or coating in order to protect it, to insulate it from the other parts of the device, or to provide a seal.

In some embodiments, the helical arm is not coiled in direct contact with the feedline. It may, for example form turns at a position radially displaced from the feedline. The helical arm may be coiled about a substrate that supports it. Where the feedline comprises an outer insulator, this outer insulator may be the substrate for the helical arm, which may form turns around the outer insulator. Alternatively the helical arm may, for example, be coiled about a tubular substrate, such as a cooling tube positioned about the feedline.

The total number of turns (N) may be in the range of 1-12 but is not limited to integers. In optional embodiments, N is typically from 4 to 8. For each complete helical turn, the axial distance is a pitch (P), which can range from 0.7-1.5 mm, the pitch may also range from 1-1.5 mm and in an optional embodiment, the pitch (P) of the helical arm is from 1.2-1.25 mm. The number of helical loops (N) and pitch (P) can affect the output of microwave energy, the shape of the emission field and the energy absorption spectrum.

The linear arm 420 is electrically connected to the inner conductor 427 of the feedline 432 and extends distally from the distal end of the feedline 432. The helical arm 412 is disposed coaxially about the linear arm 420.

The device has a cooling system configured to pass a coolant fluid over the antenna. The cooling system is configured to pass a coolant fluid over at least a portion of the feedline and over the antenna as described in more detail below.

As shown in FIG. 4A, the helical arm 412 may be coiled on a tube 426 which may act as a support substrate, or as in this case, acts as a cooling tube which extends from the manifold (not shown), through the metal portion 445 of the shaft to the tip 428 of the antenna 452. The electrical connection between the helical arm 412 of the antenna 452 and the outer conductor of the feedline 432 passes through the tube at the junction point 436. In the illustrated example, the helical arm 412 has a length (Lha). In some examples, the overall length of the helical arm (Lha) can range from 1 mm to 18 mm, the helical arm may also range from 4 mm to 10 mm. In a optional embodiment, the helical arm ranges from 4 mm to 7 mm.

The linear arm 420 is an extension of the inner conductor 427 of the feedline 432 and is surrounded by a dielectric layer 425, except for the second portion 423, which is free of dielectric.

The linear arm of the antennas described herein is a conductor which is electrically connected to the inner conductor 427 of the feedline 432 and extends distally therefrom and optionally on an axis co-axial with the helical arm and/or the feedline 432. The conductor may be in the form of a straight wire. In a particular embodiment, the linear arm includes a first, proximal, insulated portion and a second distal non insulated portion. Typically the first portion is surrounded by a dielectric and a second portion, distal of the first portion is free of dielectric. The second portion extends to the tip of the arm. The dielectric surrounding the first portion of the linear arm may optionally extend from the distal end of the feedline. In its simplest form, the linear arm of the antenna may be an extension of the feedline's inner conductor. The dielectric may then be an extension of the dielectric disposed between the central and outer conductors of the co-axial feedline.

The linear arm and the helical arm of the antenna may be co-axial with the shaft of the ablation device, and thus the linear arm is co-axial with and extends distally from, the helical arm. As shown, the linear arm 420 of the asymmetric dipole antenna of FIG. 4A has a length L1a. The linear arm 420 includes a first portion L1 421 coated with an insulator, which is an extension of the first dielectric layer of the feedline 432 which is disposed between the inner conductor 427 and the outer conductor 430 and is not visible in this view. The linear arm 420 further includes a second portion 423 which has a length L2 422 and which is not coated with the insulator. In one embodiment, the second portion L2 422 is exposed to the circulating coolant.

In one aspect, the portion of the linear arm lacking dielectric is partially or completely inserted into the metal cap, but does not touch the cap. This can be achieved by creating an open pocket in the base of the cap into which this part of the antenna or a portion of it is inserted. The degree to which the exposed distal tip is inserted influences the shape of the distal portion of the energy field and hence the shape of the ablation zone.

Where the distance between the tip and cap is greater than 3 mm they are not considered to be sufficiently coupled to be useful in shaping the ablation, particularly at 2.45 GHz.

The linear arm 420 may have a length (L1a) of from 4 mm to 14 mm and optionally from 8 mm to 10 mm. The second (e.g., exposed) portion 423 may have a length (L2) of from 0.1 mm to 2 mm, optionally from 0.3 mm to 0.5 mm.

Thus in an optional embodiment, the helical arm 412 of the antenna is in the form of a ribbon, having a length (Lha) of 1 mm to 18 mm and comprises 1 to 14 turns, the linear arm 420 of the antenna is 4 mm to 14 mm long and has a second, distal portion 423 lacking dielectric of 0.1 mm to 3 mm long, the portion lacking dielectric separated from the base of the cap by 0.2 mm to 3 mm.

In a particular embodiment, the helical arm 412 of the antenna is in the form of a ribbon, having a length (Lha) of 4 mm to 10 mm and comprises 4 to 8 turns, the linear arm 420 of the antenna is 7 mm to 10 mm long and has a second, distal portion 423 lacking dielectric of 0.3 mm to 0.5 mm long, the portion lacking dielectric separated from the base of the cap by 1 mm to 2 mm.

In a particular embodiment, the helical arm 412 of the antenna is in the form of a ribbon, having a length (Lha) of 4 mm to 6 mm and comprises between 3 to 5 turns. The linear arm 420 is 7 mm to 10 mm long having a second, distal portion 423 lacking dielectric 0.3 mm to 0.5 mm long, the portion lacking dielectric separated from the base of the cap by 1 mm to 2 mm, optionally by at or about 1.5 mm.

Where the shaft has a non-metallic portion (e.g., ceramic portion 402), the non-metallic portion may extend axially to cover the antenna and thus is at least co-extensive with the radiating portion of the antenna. In one embodiment the non-metallic portion extends at least from the proximal most point of the helical arm to the distal end of the shaft (e.g., the point of attachment of the tip of the device). The non-metallic portion extends axially and circumferentially such that the shaft may be non-metallic between the proximal and distal extent of the non-metallic portion.

A cap may be configured to seal the distal end of the device to prevent coolant leakage or tissue fluid penetration. The cap may be manufactured as a separate part and may be configured to be attached to the shaft. The cap may be configured to aid insertion into tissues and to penetrate the skin of a patient and so may, for example, come to a distal point, or be configured as a trocar. The cap 440 shown in FIG. 4A includes a trocar tip. The trocar tip of cap 440 can be made with stainless steel and/or ceramic.

In some examples, the cap may be made of any suitable biocompatible material such as a biocompatible polymer, composite, ceramic or metal such as stainless steel. Where the cap is metal, the cap and the distal end of the antenna (i.e. the distal end of the linear arm of the antenna) may be configured, to be electromagnetically coupled. This can be done by adjusting the distance between the distal tip of the antenna and the cap so that they become electromagnetically coupled at the frequency and at the power at which the antenna is intended to operate. This effect can be used to tune the shape of the distal portion of the energy field generated by the antenna and hence the shape of the ablation zone. The cap and antenna need not, however be so coupled, i.e. the antenna may be electromagnetically decoupled from the cap. The tip and cap may not touch. In practice the gap between the tip and the cap is 0.2 mm or greater, particularly 0.2 mm to 3 mm and optionally 1 mm to 2 mm or more specifically about 1.5 mm.

The shape of the energy field and hence the ablation volume can also be influenced by the provision of a metallic sheath concentric with the feedline. The sheath may be cylindrical and extends over at least a portion of the feedline proximal to the antenna. The sheath may also extend over at least a portion of the antenna, but may terminate at a point proximal to the distal most point of the helical arm of the antenna and does not extend over the antenna. Optionally the gap between the sheath and the distal most portion of the helical arm is at least 0.1 mm. The gap may be, for example, between 0.1 to 2 mm or 0.1 to 1 mm, optionally it is at or about 0.5 mm. The sheath is optionally not placed on the outer surface of the shaft, but may be radially displaced from the feed line and co-axial with it. It may be placed between the feedline and the inner wall of the shaft. In one arrangement, the metal sheath may be an adaptor sleeve as described elsewhere herein.

A coolant chamber may be defined between the inner walls of the device shaft. The chamber may be bounded distally by the cap and may be bound proximally by one or more proximal seals or walls, which close the coolant chamber proximally. The one or more seals may be formed at the manifold or at a point between the manifold and the proximal portion of the helical arm of the antenna. The cooling system comprises at least one coolant inlet conduit configured to deliver coolant to the coolant chamber and at least one coolant outlet conduit to remove coolant from the chamber. The coolant inlet and coolant outlet conduits typically pass through the proximal seal. In one approach, the coolant inlet conduit is a coolant inlet tube configured to deliver coolant to a position adjacent to and radially outward of the antenna and or feedline. In this case, the coolant inlet tube may be disposed within the coolant chamber between the antenna and the inner wall of the shaft. It may be displaced radially outward of the feedline.

In an alternative arrangement the cooling system comprises a coolant inlet conduit and a coolant outlet conduit, each conduit arranged about at least a portion of the feedline and a portion of the antenna. Each conduit arranged in the form of a helix, the coolant inlet conduit and the coolant outlet conduit being interdigitated one with the other to form a double helix. In one particular arrangement the cooling system comprises a pair of helical dividers arranged about the feedline and at least a part of the antenna in a double helix, each divider extending radially outward, towards the inner wall of the shaft and extending radially inward towards the antenna and/or the feedline such that the coolant inlet conduit and the coolant outlet conduit are formed between the two dividers and the coolant inlet conduit and coolant outlet conduit form a double helix. The dividers may be in the form of filaments or ribbons, or a combination of both. Where the dividers comprise a ribbon, the ribbon may be generally perpendicular to the inner shaft wall. The filaments may be formed of metal or of a resilient polymer. The dividers may extend to seal against the inner wall and at least a portion of the antenna and/or feedline.

The cooling system may additionally comprise a coolant mixing chamber in fluid communication with both the coolant inlet and coolant outlet conduits, such that the coolant inlet and coolant outlet are in fluid communication via the coolant mixing chamber. The coolant mixing chamber may be configured to allow coolant to pass over at least a portion of the antenna, particularly at least a portion of the linear arm of the antenna. The coolant mixing chamber is particularly configured to allow coolant to pass over the distal portion of the linear arm of the antenna and at least a portion of the cap.

Alternatively, the cooling system comprises a coolant chamber defined between the inner walls of the device shaft. The chamber may be bounded distally by the cap and proximally by a seal between the manifold and the shaft, or at some point distal from the manifold and between the antenna and the manifold as previously described. The coolant chamber surrounds the antenna and at least a distal portion of the feedline.

In an embodiment, (see for example FIG. 4A) the cooling system further comprises a cooling tube disposed about the feedline. The cooling tube may extend distally about the feedline and may be co-axial therewith. The cooling tube may divide the coolant chamber into a first cooling conduit 448 and a second cooling conduit 460, the first cooling conduit disposed between the feedline and the inner wall of the cooling tube and the second cooling conduit disposed between the outer wall of the cooling tube and the inner wall of the device shaft. The cooling tube may extend over the distal portion of the feedline and extends distally about at least a portion of the antenna, optionally the cooling tube extends at least to the tip of the linear arm of the antenna. A variety of materials are suitable for the cooling tube, but it may be non-metallic. Conveniently the cooling tube may be made of a thermoset polymer such as a polyimide or of a thermoplastic polymer resin such as polyethylene terephthalate (PET) or a fluropolymer such as polytetrafluroethylene (PTFE), or of a PAEK such as PEEK.

As described elsewhere herein, in the example of FIG. 4A, the helical arm is coiled on a cooling tube 426. In an embodiment, the cooling tube 426 is disposed about the linear arm 420 of the antenna. It defines a first cooling conduit 448 between the inner wall 454 of the tube 426 and the feedline 432 and a second cooling conduit 460 between the outer wall 455 of the tube 426 and the inner wall of the shaft 453. Coolant may be pumped through the space between the tube 426 and the feedline 432 to a mixing chamber 429 between the tube 426 and the cap 440 and returns in the space between the outside of the tube 426 and the ceramic portion of the shaft, through the space 411 between the inside of shaft and the adaptor 410 and back down the metal portion 445 of the shaft to the manifold.

The helical arm of the antenna may be disposed within the first cooling conduit, for example the distal portion of the feedline may comprise a second insulator as described above, and the helical arm of the antenna is wound directly about the feedline, the second insulator extending axially at least between the helical arm and the second conductor of the feedline. In this case, the cooling tube may extend to cover a portion of the helical arm, and may cover the helical arm and a portion of the linear arm, particularly the cooling tube may extend at least to the distal end of the antenna, such that the first cooling conduit extends at least to the tip of the antenna.

Otherwise the cooling tube extends to cover the distal portion of the feedline and a portion of the linear arm, and the cooling tube may extend at least to the distal end of the antenna, such that the first cooling conduit extends at least to the tip of the antenna.

The cooling system may additionally comprise a coolant mixing chamber in fluid communication with both the first cooling conduit and the second cooling conduit, such that the first cooling conduit and the second coolant are in fluid communication via the coolant mixing chamber. The coolant mixing chamber may be configured to allow coolant to contact a portion of the cap.

Either the first or the second cooling conduit may act as the coolant input conduit or coolant output conduit. The first and second cooling conduits are open at the distal end allowing the coolant to circulate through the coolant mixing chamber between the distal end of the cooling tube and the base of an applicator cap.

The cooling tube may extend proximally towards the manifold. The first cooling conduit and second cooling conduits are in fluid communication with coolant input and output connectors of the manifold, for the supply of coolant and discharge of coolant during use.

In a particular approach, the helical arm of the antenna, optionally in the form of a ribbon, is wound about the cooling tube. In this case, the helical arm is in electrical contact with the outer conductor of the feedline at the junction point and extends distally in a series of turns about the cooling tube as described above. In this case, the cooling tube may extend at least to the junction point of the antenna and feedline, may further extend to cover at least a portion of the linear arm, optionally the cooling tube extends to the tip of the linear arm, such that the first cooling conduit extends at least to the tip of the antenna. The electrical contact between the distal end of the helical arm and the outer conductor of the feedline may pass through the cooling tube.

In this approach the outer insulator may not extend over the distal portion of the feedline. For example, it may not extend over at least the portion which extends from a point on the feedline immediately proximal of the helical arm of the antenna to the junction point. The outer insulator may be absent from the entire feedline within the shaft of the ablation device.

In embodiments in which the cooling system comprises a cooling tube as described above, the helical arm may be either a wire or a ribbon, but is optionally a ribbon. The helical arm may be in the form of a cylindrical conductor, having a helical gap running from its proximal end to its distal end to give a helical conductor having a planar conductor surface disposed about the feedline and may be co-axial with it.

The cooling systems described herein pass a coolant (e.g., water) over the feedline and at least a portion of the antenna, optionally the whole antenna. It is not necessary to insulate the antenna from the coolant for normal operation. In some embodiments described herein parts of the feedline are lacking an outer insulator surrounding the feedline. The feedline may be lacking insulator between the manifold and the junction point or its whole length within the device shaft. The helical arm of the antenna may also lack any insulation, particularly where it is wound about a cooling tube.

The ablation devices described herein may additionally comprise one or more temperature sensors, such as a thermocouple, to measure the temperature at points along the shaft. Typically a thermocouple may be located within the cooling system and configured to measure the temperature of the coolant or of other parts of the device such as the feedline or device shaft during operation of the device. The microwave tissue ablation device 400 of FIG. 4A may include a temperature sensor 450 for example housed next to the internal adaptor 410, having an electrical connection 451 via the hub to the control unit.

As described elsewhere herein, ablation devices such as those described herein typically comprise a proximal manifold as discussed briefly above. The manifold typically comprises connectors for connecting the feedline to an energy supply line and for connecting electrical devices within the device shaft to control systems. Such connectors may be permanent or demountable. The manifold may also comprise coolant manifold with input and output connectors for connecting the coolant input to a coolant supply and the coolant output to waste or recirculating system. The manifold may also form part of a handle configured to provide a firmer grip for a surgeon to handle the tissue ablation device.

Figure 5:
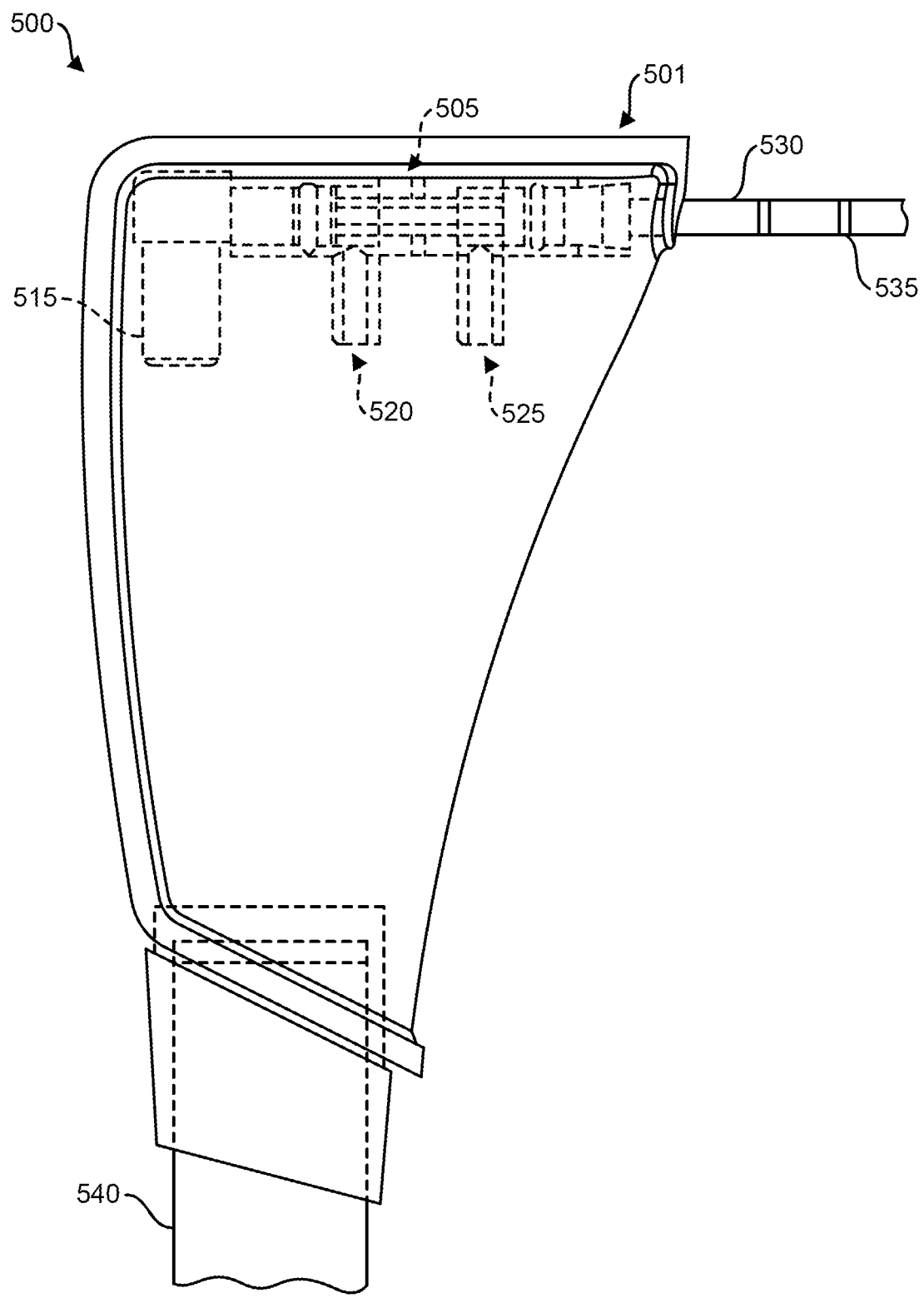
FIG. 5 is a side view of a microwave tissue ablation device according to one embodiment of the disclosure.

FIG. 5 is a side view of a microwave tissue ablation device according to one embodiment of the disclosure. The ablation device 500 includes a handle 501. The handle 501 houses a manifold 505.

The manifold 505 electrically connects the power source (not shown) and the tissue ablation probe 530 through the coaxial cable connector 515. The tissue ablation probe 530 includes markings 535 configured to inform surgeons of the depth of probe penetration during surgery.

The manifold 505 also fluidically connects the coolant source (not shown) and the tissue ablation probe 530. The manifold 505 includes a coolant inlet 520 and a coolant outlet 525. The coolant inlet 520 is fluidically connected to the coolant inflow conduit and the coolant outlet 525 is fluidically connected to the coolant outflow conduit.

The tissue ablation device 500 further includes tubular housing 540 that houses the electric wires and fluid tubes.

Figure 6A:
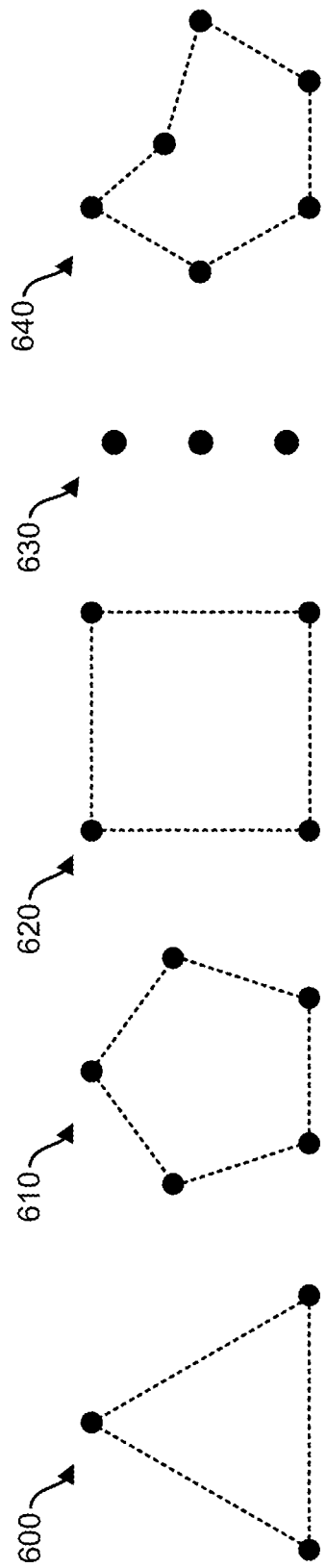
FIG. 6A shows a plan view of a plurality of microwave ablation needle configurations.

As discussed elsewhere herein, a plurality of ablation devices, such as microwave tissue ablation device 300, can be used simultaneously to perform ablation processes. Such ablation devices may be arranged in a variety of ways. FIG. 6A shows a plain view of a plurality of microwave ablation needle configurations. In an example, microwave ablation devices can be positioned equidistant from each other, such as in arrangement 600. Needles can be arranged in a regular polygon formation, such as in arrangements 600, 610, and 620. Positioning the ablation devices equidistant from one another may advantageously provide an approximately symmetric net ablation volume formed by the plurality of ablation devices. Additionally, arranging the ablation devices in a regular polygon formation may provide an approximately spherical net ablation volume formed by the plurality of ablation devices. Alternatively, other arrangements, a plurality of devices arranged in a line such as in arrangement 630, or in an irregular shape such as in arrangement 640. Ablation devices can be arranged in a plurality of configurations to provide a desired ablation volume appropriate for a particular operation.

Figure 6B:
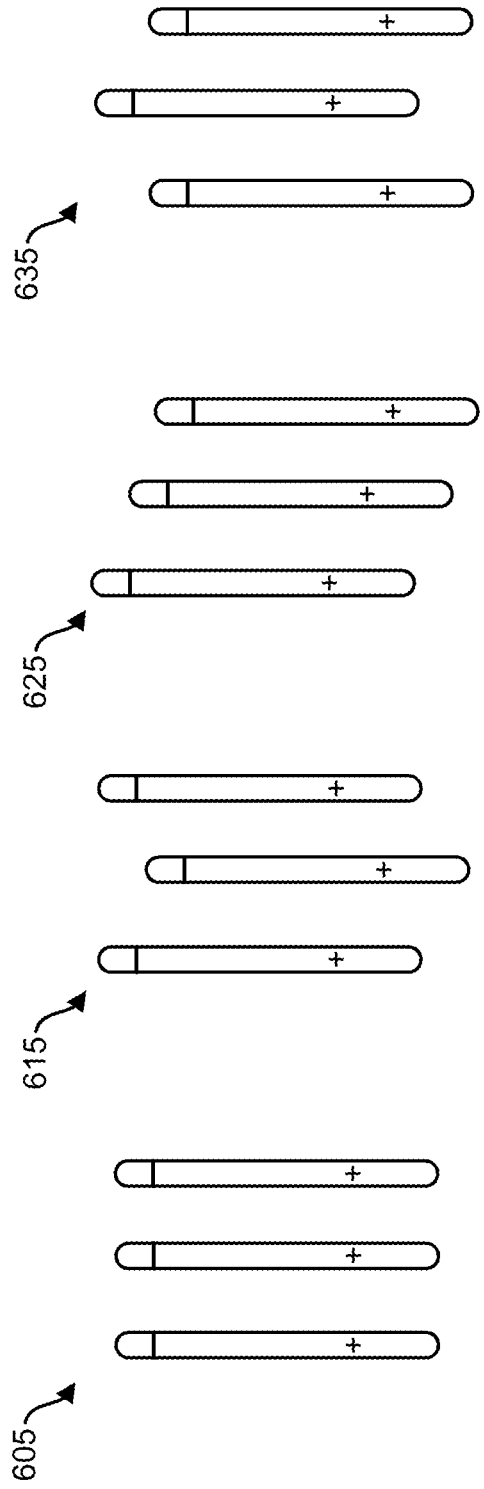
FIG. 6B shows an elevation view of a plurality of ablation devices at different depth arrangements.

In addition, such devices can be inserted to the same or different penetration depths. FIG. 6B shows an elevation view of a plurality of ablation devices at different depth arrangements. Ablation devices, such as microwave tissue ablation device 300, can be inserted to particular depths, for example, as gauged by markings 311. In some configurations, the devices are inserted to approximately the same depth, such as in arrangement 605. In other examples, devices can be inserted to different depths, such as in arrangements 615, 625, and 635. Similar to different plan arrangements, ablation devices can be arranged in a plurality of configurations to provide a desired ablation volume appropriate for a particular operation.

During operation involving one or more ablation devices, a console (e.g., 102) can actuate a pump (e.g., 148*a*) to cause a coolant to flow from a coolant source (e.g., 140) to each of the one or more ablation devices (e.g., 400). For each ablation device, coolant can flow through a coolant line (e.g., 114*a*), a coolant inlet (e.g., 520), a first cooling conduit (e.g., 448), a second cooling conduit (e.g., 460), and a coolant outlet (e.g., 525). In some examples, coolant line (e.g., 114*a*) provides a return path to receive fluid from the coolant outlet (e.g., 525), for example, in a recirculation system in which coolant is recirculated to the coolant source. In an embodiment, coolant can flow through such a flow path to provide cooling to the ablation device.

As described herein, a controller (e.g., 106), for example, within a console (e.g., 102) receiving the ablation device (e.g., 400) can be used to control the fluid flow through the ablation device as well as the microwave energy emitted from the ablation device.

Coolant can also act as a dielectric to couple microwave radiation emitted from a microwave antenna (e.g., 452) to surrounding tissue when the microwave ablation device is inserted in a patient. In an embodiment, coolant flows through the needle during a treatment ablation process at a treatment ablation flow rate. Coolant flowing through the needle at the treatment ablation flow rate can couple the microwave energy emitted from the needle to the tissue surrounding the needle and impact the penetration depth of the microwave energy into the tissue. Reducing the flow of coolant can result in an increase in coolant temperature and impact the coupling of the microwave energy to the surrounding tissue, resulting in a smaller ablation zone. Additionally or alternatively, reduced coolant flow can reduce the ability of the needle to draw heat away from tissue proximate the needle, resulting in more localized heating of tissue proximate to the needle compared to higher flow rates. The increased temperature of the tissue proximate the needle can impact the coupling of the microwave energy to the tissue.

In some examples, due to differences in the size and/or shape of ablation zones due to differences in the flow rate of a coolant flowing through a needle, during an ablation procedure, systems can provide a sufficient coolant flow rate to efficiently couple the needle to the surrounding tissue to achieve a desired ablation zone. However, in some cases, manipulating the shape of the ablation zone can be leveraged to provide additional system functions and features.

In an example, a narrow ablation zone can be used to cause the needle to stick to a medium in which the needle is inserted, such as patient tissue. A narrow ablation zone can be used to heat tissue proximate the needle, which can denature the tissue adjacent the tissue to the point of the tissue adhering to the needle, without damaging additional tissue. Moreover, if the needle is adhering to tissue to be ablated, the tissue that is denatured via the narrow ablation zone will ultimately be ablated during the operation, and therefore the denaturing of the tissue proximate the needle does not damage any excess tissue beyond that which is intended for ablation.

Adhering a needle to tissue can provide several advantages. In some cases, during or after placement for an ablation needle, the needle can be at risk of moving. For example, a clinician may be unable to physically hold the needle in place after placement, as the clinician may be required to perform additional tasks, such as inserting additional needles or performing other operations. In the meantime, a patient may move or be moved, causing the needle to shift within the patient. In some cases, needles may move with patient respiration, such as needles positioned in a lung, liver, diaphragm, or the like. Additionally or alternatively, a needle or associated cartridge or adjoining cable may be accidentally bumped or simply move due to gravity, causing the inserted needle to move out of position. Such needle movement may lead to imprecise ablation locations within a tissue, risking unnecessary damage to healthy tissue and/or incompletely ablating a target region, such as a lesion in the tissue.

Other advantages exist for adhering the needle to tissue. For instance, in some examples, a lesion may be difficult to physically pierce with an ablation needle. A clinician may insert the needle proximate to such a lesion and adhere the needle to the side of the lesion to ensure the needle is placed as close to the lesion as possible. This way, multiple needles can be positioned adjacent multiple sides of such a lesion in order to ablate the lesion from multiple sides.

Additionally or alternatively, in some cases, adhesion between tissue and a needle can be strong enough to allow a clinician to physically manipulate the tissue to improve a potential ablation zone. For example, a clinician may adhere the needle to the side of a lesion and then utilize the adhesion to maneuver the lesion away from an area that the clinician does not want to ablate, such as an organ or blood vessel, to reduce the risk of undesired damage to such structure.

In an embodiment, operating parameters of an ablation system, such as coolant flow rate and ablation power, can be adjusted via an interface (e.g., user interface 104). In such an embodiment, a clinician may manually select a coolant flow rate and ablation power for causing adhesion of a needle to patient tissue before performing an ablation procedure.

According to aspects of the disclosure, an ablation system can be pre-programmed with a "stick mode" of operation, wherein the controller controls a coolant flow and ablation power in order to cause adhesion of a needle to a patient. In some embodiment, the controller can be configured to initiate such a stick mode upon receiving an input from a user interface to perform the stick mode procedure. The stick mode of operation can be used to cause adhesion between the needle and the surrounding tissue, wherein the adhesion is strong enough to hold the needle in place against undesired, accidental movement, but is not so strong that the needle cannot be removed without damaging surrounding tissue (e.g., if the needle is to be purposely repositioned).

In addition to causing adhesion between a needle and surrounding tissue, manipulation of the ablation zone shape and size, for example, via adjusting the flow rate of coolant through the needle, can be useful for performing additional practices. For instance, in some cases, there is concern that withdrawing a needle that was inserted proximate a cancerous lesion can extract viable cancer cells along with the needle, potentially depositing such cells elsewhere in the tissue via a process known as track seeding. To combat track seeding, a system can be configured to perform a track ablation process, wherein the system performs and/or guides a user through a process to ablate tissue adjacent the needle to prevent track seeding when the needle is extracted.

Figure 7C:
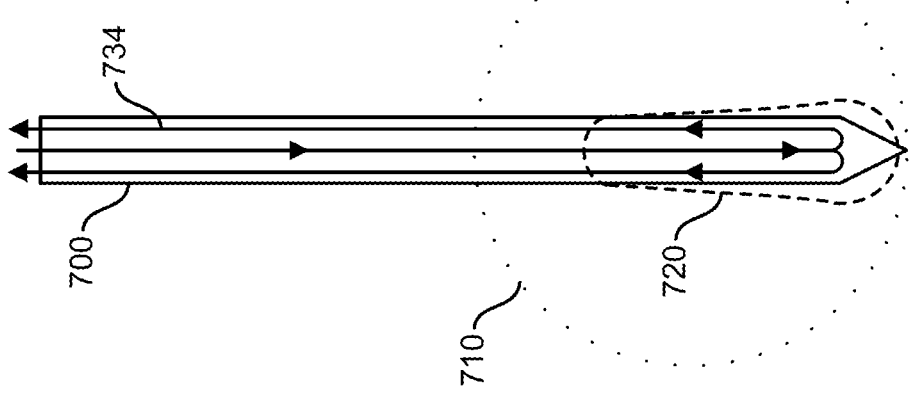
FIGS. 7A-7C illustrate example microwave ablation zones relative to a microwave ablation needle resulting from different coolant flow rates.
Figure 7B:
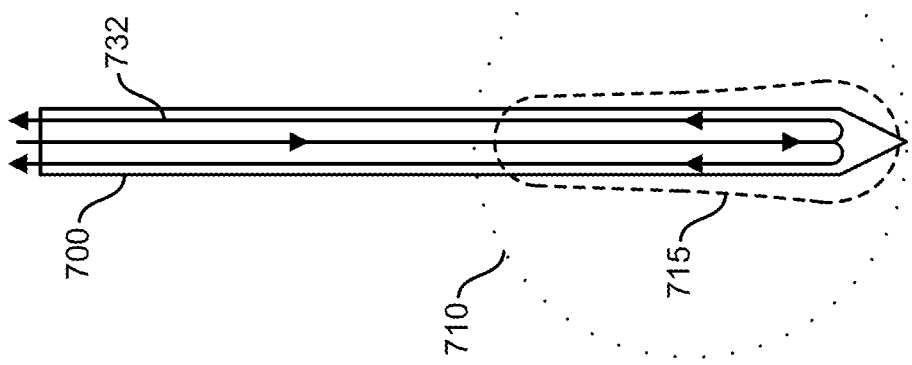
Figure 7A:
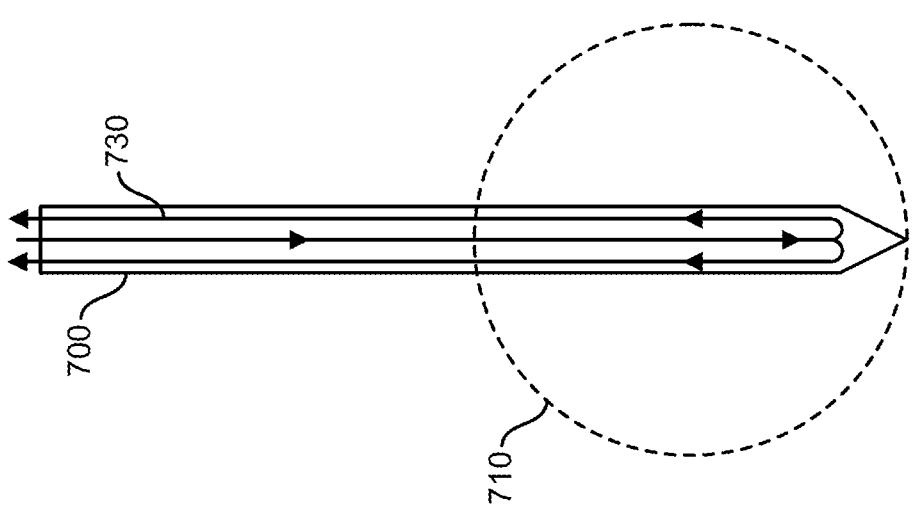

FIGS. 7A-7C illustrate example microwave ablation zones relative to a microwave ablation needle resulting from different coolant flow rates. FIG. 7A shows an ablation zone 710 associated with an ablation needle 700. Coolant 730 flows through the needle at a treatment ablation flow rate. In some examples, the treatment ablation flow rate is between approximately 70 ml/min and 150 ml/min. More specifically, in some such embodiments, the treatment ablation flow rate is between approximately 95 ml/min and 120 ml/min. In an example embodiment, the treatment ablation flow rate is approximately 110 ml/min. In the example of FIG. 7A, the coolant flows into the needle through a first cooling conduit and out of the needle through a second cooling conduit, the first and second cooling conduits being concentric similar to first cooling conduit 448 and second cooling conduit 460 shown in FIG. 4B. Ablation zone 710 is approximately spherical.

FIG. 7B shows an ablation zone 715 associated with an ablation needle 700 receiving the same amount of ablation power as the needle of FIG. 7A and having a reduced coolant flow rate when compared to the needle of FIG. 7A. Coolant 732 flows through the needle in FIG. 7B at a flow rate lower than the treatment ablation flow rate of FIG. 7A. In some examples, the lower flow rate is between approximately 45 ml/min and 75 ml/min. In an example embodiment, the flow rate is approximately 60 ml/min. Similar to FIG. 7A, in the example of FIG. 7B, the coolant flows into the needle through a first cooling conduit and out of the needle through a second cooling conduit, the first and second cooling conduits being concentric similar to first cooling conduit 448 and second cooling conduit 460 shown in FIG. 4B. In some cases, thermal conduction from tissue heated from microwave emission can contribute to the ablation zone 715 shown in FIG. 7B. For example, in some embodiments, reduced flow rate of the coolant through the needle can result in increased tissue temperature proximate the needle. This can be useful to ablate tissue proximate the needle, for example, during a track mode ablation.

FIG. 7C shows an ablation zone 720 associated with an ablation needle 700 receiving the same amount of ablation power as the needle of FIGS. 7A and 7B and having a lower coolant flow rate when compared to the needles of FIGS. 7A and 7B. Coolant 734 flows through the needle in FIG. 7C at a flow rate lower than the treatment ablation flow rate of FIGS. 7A and 7B. In an embodiment, the lower coolant flow rate is between approximately 10 ml/min and approximately 30 ml/min. In some such examples, the lower coolant flow rate is between approximately 18 ml/min and 22 ml/min.

Similar to FIGS. 7A and 7B, in the example of FIG. 7C, the coolant flows into the needle through a first cooling conduit and out of the needle through a second cooling conduit, the first and second cooling conduits being concentric similar to first cooling conduit 448 and second cooling conduit 460 shown in FIG. 4B.

As described with respect to FIG. 7B, lowered coolant flow rate can cause increased heating of the tissue proximate the needle. In some examples, even lower flow rates can increase tissue temperature proximate the needle more quickly, which can be useful, for instance, to rapidly heat the tissue to initiate adhesion between the needle and the tissue, such as in "stick mode" discussed elsewhere herein.

Ablation zone 710 representing the ablation zone resulting from the ablation coolant flow rate (as illustrated in FIG. 7A) is overlaid onto FIGS. 7B and 7C for reference. As shown, the ablation zones 715 and 720 are generally elongate in the longitudinal direction of the needle 700, and are narrower than ablation zone 710. In an embodiment, ablation zones 710, 715, and 720 corresponding to an ablation coolant flow rate, a reduced coolant flow rate, and a further reduced coolant flow rate, respectively, result from applying the same ablation power to the needle, where the different shapes and sizes of ablation zones result from the different coolant flow rates. For instance, in an embodiment, reducing the coolant flow rate changes the coupling of the microwave energy between the needle and the surrounding tissue, for example, due to localized heating of the tissue, resulting in different ablation zones, such as zones 710, 715, and 720 shown in FIGS. 7A, 7B, and 7C.

As described elsewhere herein, in some examples, reduced coolant flow rates can result in less cooling of the tissue immediately proximate the tissue, which may cause the tissue to heat more quickly and/or to a higher temperature. Higher tissue temperatures can impact the transmission of microwave energy from the ablation device into the tissue, which can contribute to the change in shape of the illustrated ablation zones. It will be appreciated that ablation zones may change in size and shape over time as additional tissue is ablated and conduction heats additional tissue not directly heated by microwave energy. In an example, ablation zone 720 results from applying a same amount of ablation power to tissue as does ablation zone 710, though with a much lower coolant flow rate and for a shorter amount of time.

In an example, the energy density within the ablation zones 715 and 720 are higher than that in ablation zone 710. For instance, in an example, ablation zone 715 receives approximately the same amount of power compared to ablation zone 710, but to a smaller volume. In another example, ablation zone 715 receives a smaller amount of power than ablation zone 710, but the ratio of received power in zone 715 to received power in zone 710 is greater than the ratio of the volume of zone 715 and the volume of zone 710.

The relative sizes and shapes of ablation zones 710, 715, and 720 in FIGS. 7A, 7B, and 7C illustrate examples generally showing that the shape of ablation zones from microwave energy delivered by a microwave ablation needle may differ due to changes in coolant flow rate. The ablation zones 710, 715, and 720 along with needle 700, are not necessarily shown to scale, and in practice relative sizes and shapes of the ablation zones and needle may vary among different embodiments. In some cases, relative sizes of ablation zones 710, 715, and 720 can vary based on an amount of time that ablation power is provided to an ablation device.

In some examples, in addition to changing the flow rate of the coolant through the needle, changing the amount of power applied to the needle can also impact the resulting ablation zone. In some examples, maintaining a constant ablation power while decreasing the flow rate of the coolant can result in narrowing the ablation zone, such as shown in FIGS. 7A-7C. Additionally or alternatively, in some examples, maintaining a constant flow rate while modulating the amount of power applied to the ablation device results in changing the size of the ablation zone while maintaining approximately the same shape. Thus, in some examples, ablation zone sizes and shapes can be achieved by modulating the ablation power and the coolant flow rate.

Figure 8:
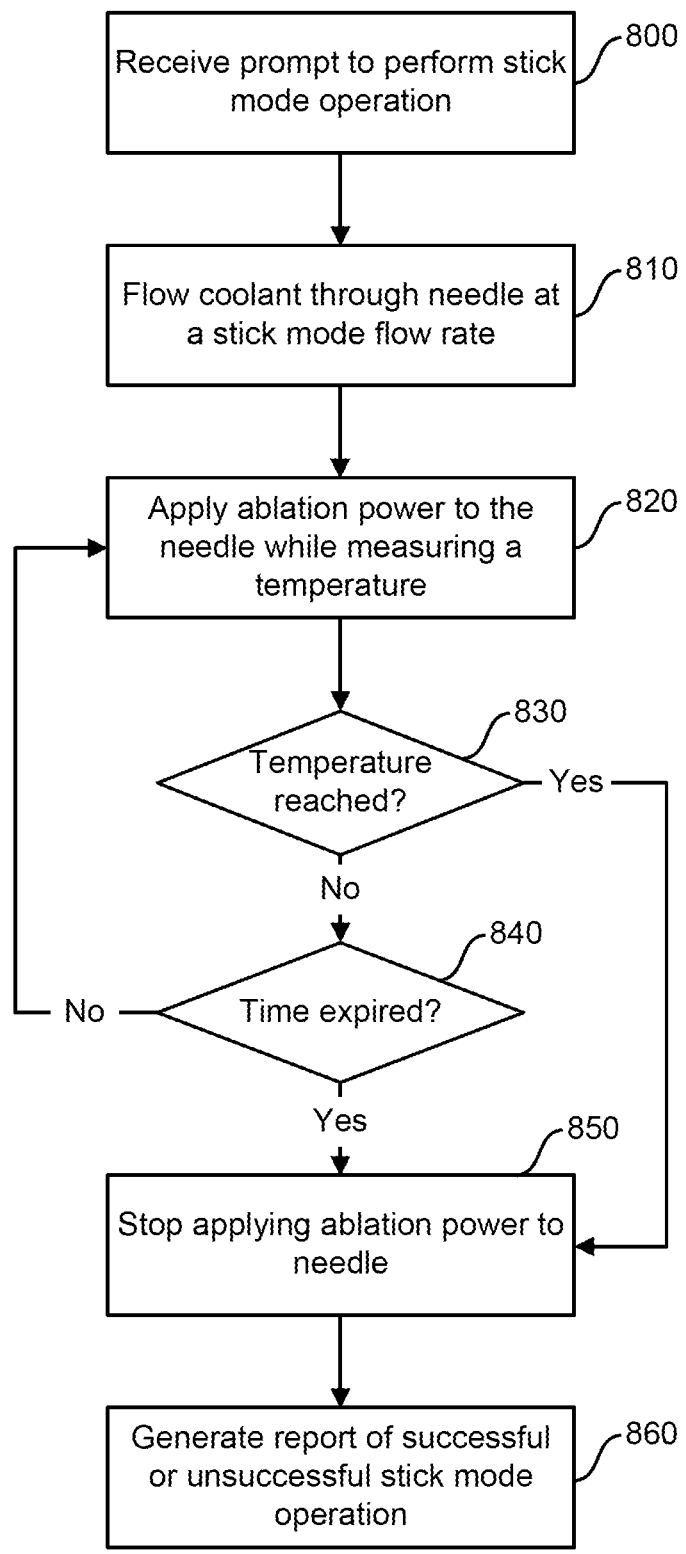
FIG. 8 is a process flow diagram showing a process, executable by a controller, for performing a stick mode procedure according to an embodiment of the disclosure.

FIG. 8 is a process flow diagram showing a process, executable by a controller, for performing a stick mode procedure according to an embodiment of the disclosure. The process includes receiving a prompt to perform stick mode operation (step 800), for example, via a user interface. After receiving the prompt (step 800), the process includes flowing coolant through an ablation needle at a stick mode flow rate (step 810) and applying ablation power to the needle while measuring a temperature (step 820). In an example, the stick mode flow rate is approximately 20 ml/min (e.g., 15-25 ml/min) and the applied power is approximately 45 W-90 W.

In an example, the amount of ablation power applied in step 820 is the same as or approximately the same as the amount of power used during an ablation process. The coolant can provide cooling to the needle so that the needle itself does not heat up to a dangerous temperature (e.g., dangerous to a patient or risking damage to the needle), but can be at a lower flow rate when compared to that in an ablation process so that tissue temperature proximate the needle heats more quickly than in a traditional ablation process and the ablation zone surrounding the needle is restricted to a smaller area, for example, as illustrated in FIGS. 7A and 7C. Therefore, an ablation process and a stick mode process may be carried out with the same level of applied power (45 W-90 W), but the coolant flow rate for the stick mode process is reduced relative to the ablation process. Thus, the absolute level of applied power and the absolute coolant flow rate depends on the needle. But, for a given needle, one may merely modulate the coolant flow in order to switch between a stick mode operation (lower flow) and an ablation process (higher flow).

During the application of ablation power, the temperature can be monitored to determine if a desired temperature has been reached (step 830). In some examples, monitoring the temperature is performed using a temperature measurement device, such as a thermocouple. The device can be positioned within the needle, for example, in the coolant flow path, on the outside of the needle, or separately from the needle. It will be appreciated that a temperature measurement device positioned in various locations, such as within the coolant flow path or on an outer surface of the needle, may measure different temperature values when compared to a temperature measurement device positioned at a different location. For determining if the measured temperature has reached a desired temperature in step 830, the desired temperature can be predetermined based the location of the temperature measurement device. The desired temperature can correspond to a temperature that should result in denaturing the tissue surrounding the needle to cause a desired amount of adhesion between the tissue and the needle. In an embodiment, the desired temperature is 75° C. measured at a temperature measurement device within the needle (e.g., within a coolant flow path). In such an example, the temperature external to the needle will be hotter than the temperature in the flow path measured within the needle since the microwave power is heating the tissue proximate the needle and the coolant flow is cooling the needle.

If the desired temperature has been reached, the application of ablation power is stopped (step 850). However, if the desired temperature has not been reached, the running duration of the stick mode ablation can be compared to a time limit to determine whether or not an amount of time allowed for performing the stick mode operation has expired (step 840). In an example, a maximum amount of time can be set for performing stick mode operation, such as 60 seconds. Other maximum time periods may be useful too, such as 30 seconds, 2 minutes, 5 minutes, or others. If the time has not yet expired, then ablation power can continue to be applied to the needle (step 820). However, if the time has expired, power application to the needle is stopped (step 850). It is believed that, in some locations of the temperature measurement device, tissue perfusion or tissue type will make it more difficult to reach the desired temperature. In such circumstances, the microwave energy does not heat the tissue sufficiently to provide a stick mode operation proximate the temperature measurement device.

Thus, according to the process shown in FIG. 8, ablation power is applied to the needle in stick mode until a desired temperature is reached or until a time expires, whichever comes first. After the desired temperature is reached or the time expires and the ablation power is stopped (step 850), the method includes generating a report indicating whether or not the stick mode operation was successful (step 860). In an example, the determining of whether or not stick mode is considered successful is based on determining whether or not the desired temperature was reached within the allowed time. If so, then a report indicating a successful stick mode has occurred is generated, indicating that the measured temperature reached the desired level and the needle should be adhered to the surrounding tissue. However, if the time expired prior to achieving the desired measured temperature, a report indicating an unsuccessful stick mode is generated, indicating that a desired adhesion between the needle and tissue might not have been achieved.

In an embodiment, the process shown in FIG. 8 is performed by a controller (e.g., 106) and the generated report is presented to a user on a display (e.g., user interface 104). Additionally or alternatively, the report can be communicated to a separate device, for example, via a communication network (e.g., via electronic mail) or other communication protocol (e.g., Bluetooth). Upon viewing the report, if the stick mode was considered unsuccessful, a user may choose to attempt to perform a stick mode operation again to achieve desired adhesion between the needle and the surrounding tissue. The report may suggest, or a user may choose, to reposition the needle for which the stick mode operation failed in order to attempt to better couple the needle to the tissue. Alternatively, whether or not the stick mode operation is deemed successful, an ablation procedure can be performed following a stick mode operation.

It will be appreciated that in various examples, steps of the process shown in FIG. 8 can be performed or omitted. For example, in an embodiment, stick mode ablation is performed for a predetermined amount of time whether or not a desired temperature is reached. In another embodiment, stick mode ablation is performed until a desired temperature is reached, regardless of the amount of time it takes to achieve the desired temperature.

Figure 9A:
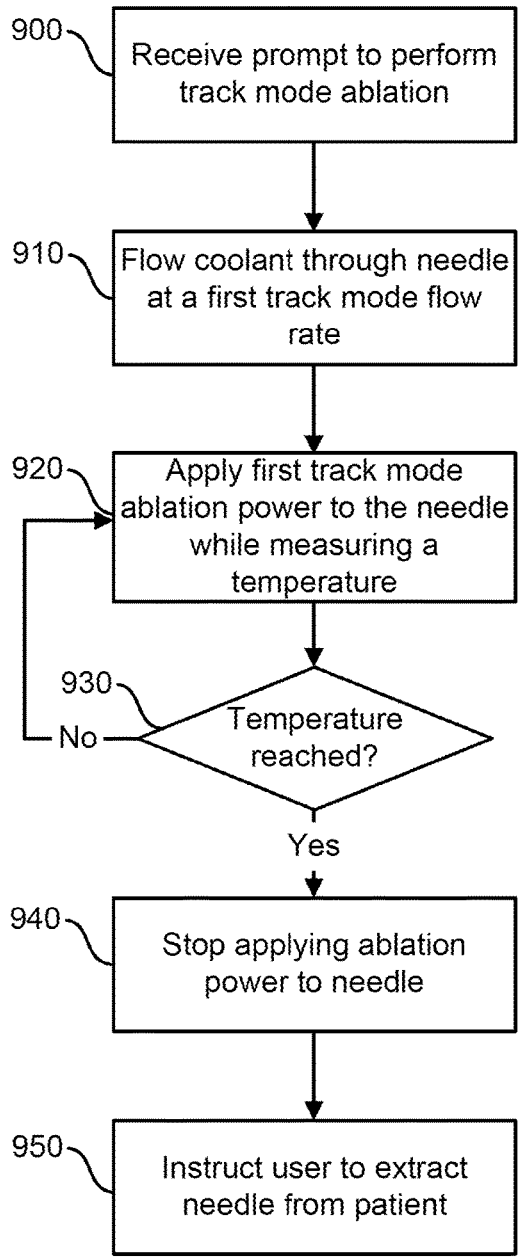
FIG. 9A shows a process flow diagram showing an example process, executable by a controller, for performing a track mode ablation process according to an embodiment of the disclosure.
Figure 9B:
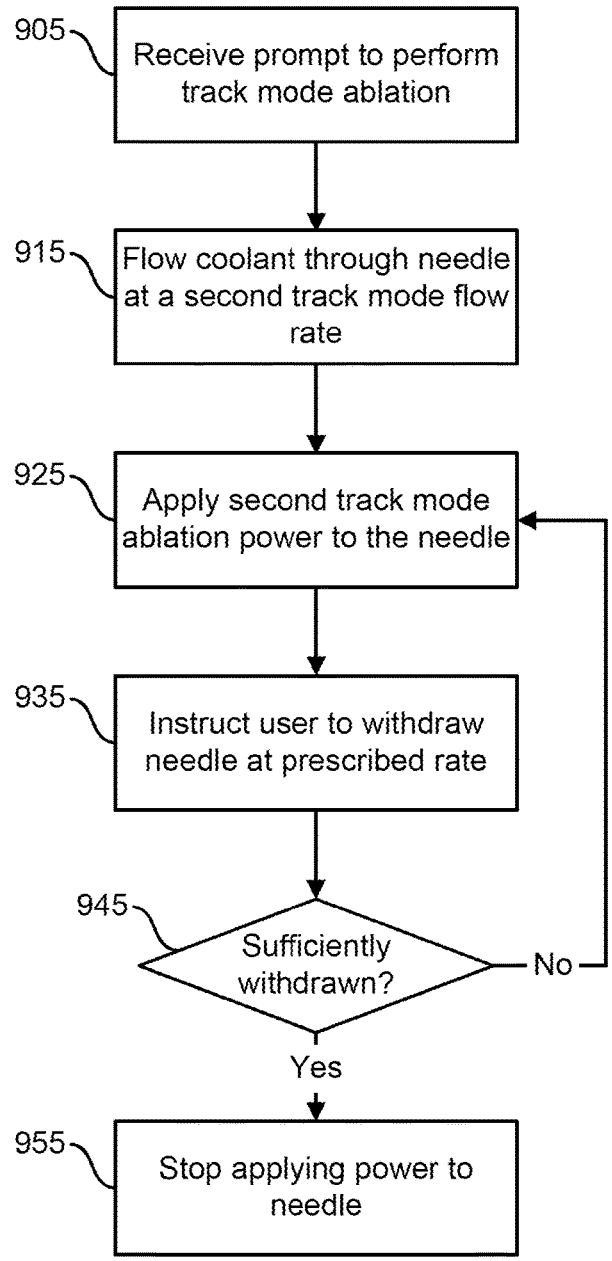
FIG. 9B shows a process flow diagram showing an alternate example process, executable by a controller, for performing a track mode ablation process according to an embodiment of the disclosure.

FIGS. 9A and 9B show process flow diagrams showing example processes, executable by a controller, for performing a track mode ablation process.

The process shown in FIG. 9A includes receiving a prompt to perform a track mode ablation (step 900). Upon receiving the prompt, the method includes flowing coolant through an ablation needle at a first track mode flow rate (step 910). The method includes applying first track mode ablation power to the needle while measuring a temperature proximate the needle (step 920). In some examples, the power applied to the needle when the first track mode coolant flow rate is lower than a treatment ablation power to prevent undesired heating of the needle or tissue caused by the reduced flow of coolant through the needle. The temperature can be monitored and compared to a desired temperature, and power can continue to be applied until the temperature is reached (step 930). Once the temperature is reached, the method includes stopping applying ablation power to the needle (step 940) and instructing a user to extract the needle from the patient (step 950).

In an embodiment the first track mode flow rate is much lower than the flow rate of the coolant during a traditional ablation process. In an example, the coolant flow rate during ablation is approximately 110 ml/min, and the first track mode coolant flow rate is approximately 10 ml/min (e.g., 5-15 ml/min). In an example, the first track mode coolant flow rate causes the shape of ablation energy emitted from the needle to elongate along the axial direction of the needle and to narrow in the radial dimension of the needle. In effect, the long, narrow ablation zone associated with the low first track mode coolant flow rate causes denaturing of a long stretch of tissue proximate the needle, destroying such cancer viable cells at risk of track seeding and creating a channel of ablated tissue from which to remove the needle.

In an embodiment, the temperature is measured at a location that is beneath the patient's skin, but is located proximal to the tip of the needle. The temperature can be monitored so that ablation is stopped when elevated temperatures caused by track ablation do not exceed a dangerous temperature too close to the patient's skin. In an embodiment, the system can determine, for example, based on a known needle insertion depth and temperature measurement device location, the maximum temperature that can be read by the temperature measurement device without excessively heating tissue close to the patient's skin. In an embodiment, the temperature measuring device comprises temperature sensor 450 shown in FIG. 4A, and ablation power is stopped when the measured temperature reaches approximately 75° C. Different temperatures can be used for different temperature sensor arrangements, which may vary by ablation device. In some examples, a console can determine an appropriate measurement temperature at which to stop ablation based on a lookup table associated with a particular needle temperature sensor configuration.

In an example of a first track mode ablation process, both power and coolant flow are lower in the first track mode ablation process than those used in a treatment ablation process. In an embodiment, applying the first track mode ablation power to the needle comprises applying approximately 35 W (e.g., in a range between 30-45 W) at the needle, as compared to about 45 W-90 W applied power at the needle for a treatment ablation process.

In another example of the first track mode ablation process, both the applied power and the coolant flow rate are much lower than what is typically used during treatment ablation. In such an example of first track mode ablation, the applied power is about 15 W (e.g., in a range between 10-20 W) and the flow rate is about 0 ml/min (e.g., 0 ml/min, or in a range of between 0-5 ml/min). Such an example of a first track mode ablation may be deemed a "no flow" example, where the needle is filled initially with fluid and any fluid flow is shut off or extremely limited while a very low ablation power is provided in the manner described in FIG. 9A.

Turning to FIG. 9B, the process shown includes receiving a prompt to perform a track mode ablation (step 905). Upon receiving the prompt, the method includes flowing coolant through an ablation needle at a second track mode flow rate (step 915) and applying a second track mode ablation power to the needle (step 925). In an embodiment the second track mode flow rate is lower than the flow rate of the coolant during a traditional ablation process. In an example, the coolant flow rate during ablation is approximately 110 ml/min, and the first track mode coolant flow rate is approximately 60 ml/min (e.g., 50-70 ml/min). As described elsewhere herein, reducing the coolant flow from the flow rate during ablation to the track mode flow rate can change the shape of the ablation zone, such as shown between ablation zones 710 and 715 in FIG. 7B.

The process includes instructing the user to withdrawn the needle at a prescribed rate (step 935). Until the needle is sufficiently withdrawn, the second track mode ablation power is applied to the needle (step 925) and the user is instructed to withdraw the needle at a prescribed rate (step 935). Once the needle is sufficiently withdrawn (step 945), the power to the needle is stopped (step 955).

In some embodiments, the prescribed rate for needle extraction (e.g., in step 935) corresponds to a particular flow rate of coolant through the needle. As described elsewhere herein, a lower flow rate can result in greater and/or faster heating of tissue proximate the needle, allowing the needle to be extracted more quickly while still sufficiently heating the tissue proximate the needle to prevent seeding.

In an embodiment, the second track mode flow rate is higher than the first track mode flow rate but lower than the coolant flow rate during an ablation process. In such an embodiment, a higher second track mode flow rate results in a less elongate ablation zone than the first track mode coolant flow rate. However, withdrawing the needle while providing ablation power to the needle results in tissue along the needle path to be ablated as the needle is extracted.

In an embodiment, the second track mode ablation power is approximately the same power as applied to the needle during the ablation process, such that the difference between performing the ablation process and the second track mode ablation process of FIG. 9B is only the coolant flow rate. In an embodiment, applying the first track mode ablation power to the needle comprises applying approximately 90 W (e.g., 45 W-90 W) at the needle.

In some embodiments, a needle is sufficiently withdrawn to stop applying power to the needle when the longitudinal path of the needle is effectively ablated to avoid tracking potentially viable cancer cells via needle motion. In some cases, a needle includes a visible marker on an outer surface thereof such that the needle is sufficiently withdrawn once the visible marker becomes visible outside of the patient. In some such examples, the user may observe when the needle is sufficiently withdrawn (step 945) and can provide an indication to the system that the needle is sufficiently withdrawn (e.g., via a user interface). The system (e.g., via the controller) can stop the application of power to the needle upon receiving the indication from the user that the needle is sufficiently withdrawn.

In some examples, the controller of the system is configured to automatically determine when the needle has become sufficiently withdrawn. In an embodiment, the controller is configured to track motion of the needle via a position sensing mechanism, and can determine when the needle has become sufficiently withdrawn based on the position of the needle relative to the patient's skin. In another embodiment, the controller measures the rate of needle extraction and, based on the measured rate of extraction and a known initial position, calculates the time at which the needle will be sufficiently withdrawn. In another embodiment, the controller calculates the time at which the needle would be sufficiently withdrawn assuming the needle is withdrawn at the prescribed rate (e.g., the instructed rate of step 935).

In an embodiment, withdrawing the needle at a prescribed rate corresponds to a steady withdrawal of the needle, for example, at approximately 0.2 millimeters per second. In another embodiment, withdrawing the needle at a prescribed rate corresponds to moving the needle a prescribed distance after a prescribed time, such as withdrawing the needle approximately 1 centimeter every 5-20 seconds. For instance, a user interface connected may display a timer that counts time through successive time periods. At the end of each time period the user interface may signal to the user that the user is to withdraw the needle 1 centimeter, where each centimeter increment is marked on the needle.

Figure 10B:
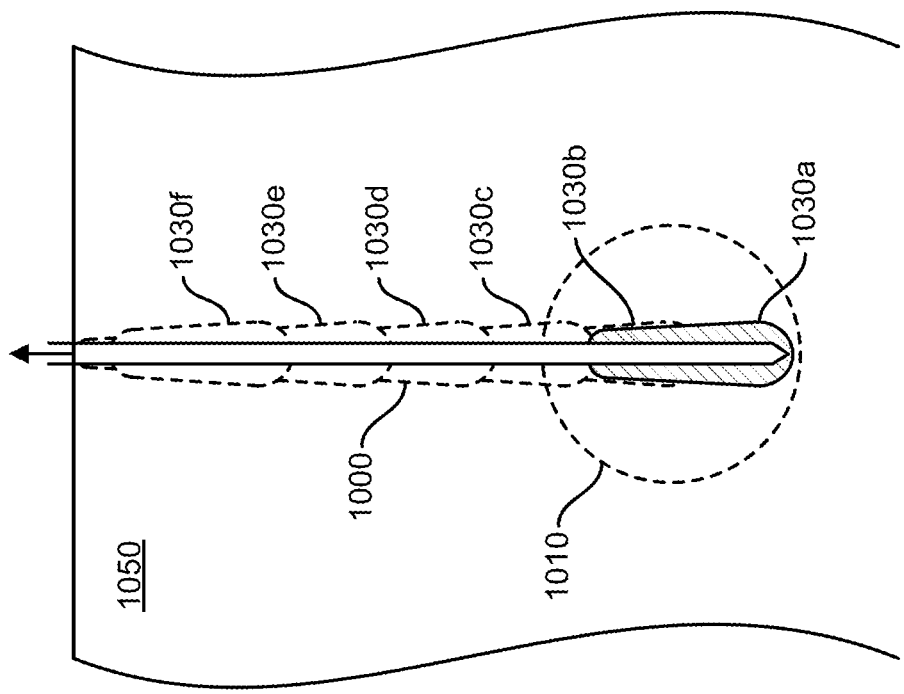
FIGS. 10A and 10B schematically show track mode ablation processes of FIGS. 9A and 9B, respectively.
Figure 10A:
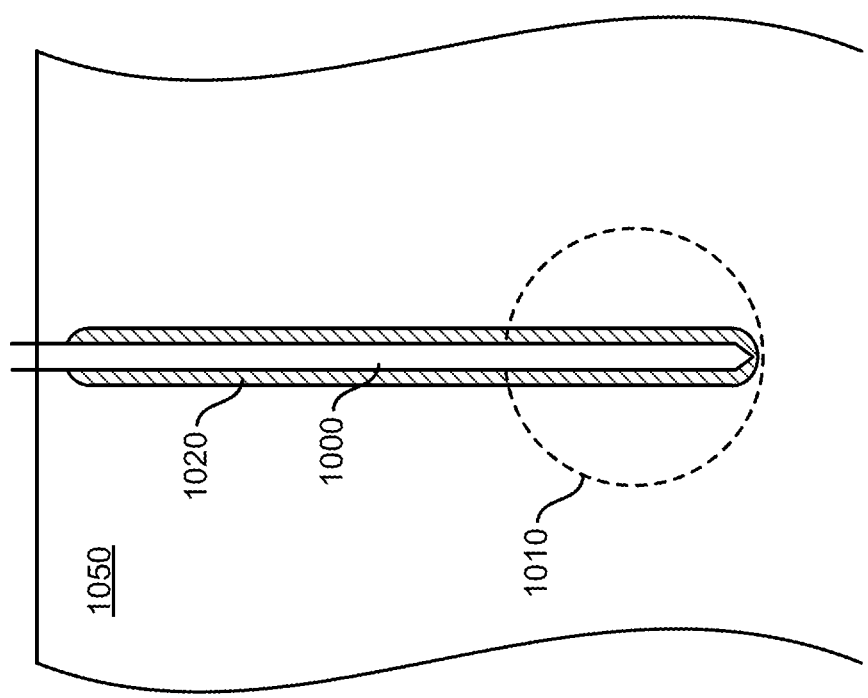

FIGS. 10A and 10B schematically show track mode ablation processes of FIGS. 9A and 9B, respectively.

FIG. 10A shows an ablation needle 1000 (e.g., a microwave ablation needle) inserted into patient tissue 1050. A treatment ablation process can be performed to ablate tissue proximate the needle 1000, for example, tissue within ablation zone 1010. After ablation is complete, the needle can be operated in track ablation mode, in which the coolant flow is adjusted to the first track mode coolant flow rate (e.g., step 910) and the first track mode ablation power is provided to the needle (e.g., step 920).

In an embodiment, the first track mode coolant flow rate and the first track mode ablation power results in ablation zone 1020, which can be used to ablate tissue along the longitudinal direction of the needle. Such ablation can denature the tissue proximate the needle 1000 and reduce the risk of track seeding.

In an example, ablation zone 1020 is caused by a coolant flow rate of 10 ml/min and an ablation power of 60 W, and is approximately 0.5 cm wide.

FIG. 10B shows an ablation needle 1000 (e.g., a microwave ablation needle) inserted into patient tissue 1050. A treatment ablation process can be performed to ablate tissue proximate the needle 1000, for example, tissue within ablation zone 1010. After ablation is complete, the needle can be operated in track ablation mode, in which the coolant flow is adjusted to the second track mode coolant flow rate (e.g., step 915) and the second track mode ablation power is provided to the needle (e.g., step 925).

In an embodiment, the second track mode coolant flow rate and the second track mode ablation power results in ablation zone 1030a, which can be used to ablate tissue proximate the needle, as shown, in a smaller volume than ablation zone 1010. The needle 1000 can be withdrawn while the coolant flows at the second track mode coolant flow rate and the second track mode ablation power is applied to the needle 1000, either at a steady rate or step-wise (e.g., as instructed in step 935). As shown, as the needle 1000 is withdrawn, the ablation zone caused by the needle 1000 moves through the tissue 1050, resulting in subsequent ablation zones 1030b-1030f. Ablation of zones 1030a-1030f results in ablation of the tissue along the needle path, which can reduce the risk of track seeding.

In an example, ablation zone 1030a is caused by a coolant flow rate of 60 ml/min and an ablation power of 45-90 W (at the needle), and is approximately 0.5 cm from the needle on all sides.

As shown, in the track ablation process shown in FIGS. 10A and 10B, tissue proximate the needle 1000 is ablated to destroy any possible cancer viable cells and prevent such cells from being moved by the needle. This can reduce the risk of inadvertent track seeding caused by a treatment ablation process in which an ablation needle (e.g., a microwave ablation needle) is inserted into patient tissue proximate a lesion and subsequently removed.

In an embodiment, the ablation power in the processes of FIGS. 9A and 9B comprises microwave ablation power, and the ablation zones in FIGS. 10A and 10B are microwave ablation zones.

As described herein, adjusting the flow rate of coolant provided to an ablation device, such as a microwave ablation needle, can change characteristics of a resulting ablation zone, such as the shape and energy density of the ablation zone. Such manipulation of the ablation zone can be used to perform various functions, such as stick mode and track mode processes. In an embodiment, a system can be configured to perform stick mode and track mode.

Figure 11:
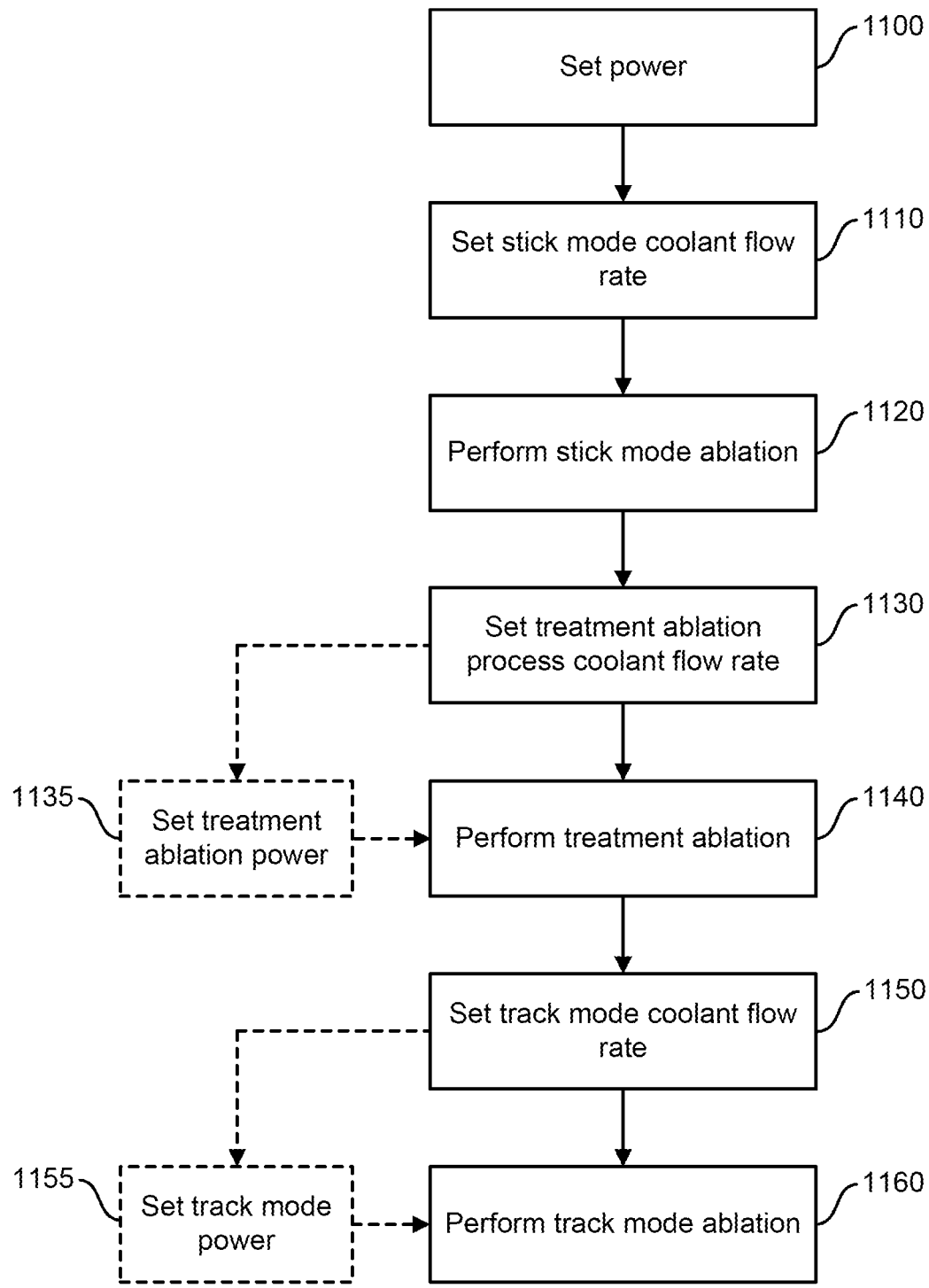
FIG. 11 shows a process flow diagram showing an example process, executable by a controller, for performing a stick mode ablation process, a treatment ablation process, and a track mode ablation process according to an embodiment of the disclosure.

FIG. 11 shows a process flow diagram showing an example process, executable by a controller, for performing a stick mode ablation process, a treatment ablation process, and a track mode ablation process. The process includes setting an ablation power (step 1100), setting a stick mode coolant flow rate (step 1110), and performing a stick mode ablation process (step 1120), for example, a process similar to that described with respect to FIG. 8).

After completion of the stick mode process in step 1120, the method includes setting a treatment ablation process coolant flow rate (step 1130) and performing a treatment ablation (step 1140). As described elsewhere herein, in an example, the treatment ablation process coolant flow rate is greater than the stick mode coolant flow rate. Thus, in some such examples, setting the treatment ablation process coolant flow rate (step 1130) comprises increasing the coolant flow rate from the stick mode coolant flow rate to the treatment ablation process coolant flow rate.

After performing the treatment ablation, the process includes setting a track mode coolant flow rate (step 1150) and performing a track mode ablation process (step 1160). In some examples, performing the track mode ablation process in step 1160 can include performing the process of FIG. 9A or 9B. As described elsewhere herein, in an example, the treatment ablation process coolant flow rate is greater than the track mode coolant flow rate. Thus, in some such examples, setting the track mode coolant flow rate (step 1150) comprises decreasing the coolant flow rate from the treatment ablation process coolant flow rate to the track mode coolant flow rate.

In an embodiment, the same ablation power is used during stick mode, the treatment ablation, and track mode. In other examples, the amount of power applied to the ablation device may be different among such modes of operation. For example, in some instances, in a track mode such as shown in FIG. 9A includes a very low coolant flow rate and a reduced amount of ablation power when compared to the treatment ablation power. Accordingly, in an example, the method includes, prior to performing a treatment ablation process (step 1140), setting a treatment ablation power (step 1135). Additionally or alternatively, in an example, the method includes, prior to performing track mode ablation (step 1160), setting a track mode power (step 1155).

Various combinations of applied power and coolant flow rate can be used to modulate the shape of an ablation zone as desired for track mode, treatment ablation, and/or stick mode. In an embodiment, a system controller can be pre-programmed with prescribed power and flow rate values for performing stick mode and track mode processes. Stick mode and track mode can be initiated manually by a user, for example, via user interface, and the controller can act to provide the predefined power and coolant flow rate to perform such processes. In some examples, power and/or coolant flow rate associated with track mode and/or stick mode may be adjustable by a user.

Table 1 below shows example predefined coolant flow rates and applied ablation powers for a plurality of modes of operation according to an embodiment. The ablation parameters result in an ablation zone within tissue proximate the needle having dimensions based on the ablation parameters.

TABLE 1

|  | Coolant Flow Rate (ml/min) | Ablation Power (W) |
| --- | --- | --- |
| Stick Mode Ablation | 15-25 | 45-90 |
| Treatment Ablation | 100-120 | 45-90 |
| Track Mode Ablation (Stationary) | 5-15 | 30-45 |
| Track Mode Ablation (Stationary, No Flow) | 0-5 | 10-20 |

TABLE 1-continued

| | Coolant Flow Rate (ml/min) | Ablation Power (W) |
|---|---|---|
| Track Mode Ablation (Withdrawal) | 50-70 | 45-90 |

In an embodiment, power is applied from a power generator to a microwave antenna in a microwave ablation needle, and the coolant flows through the needle in a channel having a cross-sectional area of between approximately 0.25 square mm and 0.75 square mm. In some examples, the coolant flows through a channel having a cross-sectional area of between approximately 0.35 square mm and 0.55 square mm. In some examples, systems can be scaled to larger or smaller needles. For instance, in some embodiments, smaller microwave ablation needles can operate in various modes using lower levels of power and lower coolant flow rates compared to examples described herein. Similarly, larger microwave ablation needles can operate in various modes using higher levels of power and higher coolant flow rates compared to examples described herein.

In an embodiment, systems can be pre-programmed with different sets of parameters for performing different stick mode and/or track mode processes, for example, for different types of tissue. In an embodiment, a system can be configured to receive an input selecting a type of tissue for ablation (e.g., a particular organ). In an example, the type of tissue is selectable from predefined list of available tissue types via a user interface. Predefined ablation parameters (e.g., coolant flow rate, ablation power, etc.) for different modes of operation, such as stick mode and track mode) can be updated automatically according to the selected tissue type, such as from a lookup table stored in memory.

In an embodiment, a user selects a tissue type via a user interface (e.g., 104) and a controller (e.g., 106) establishes predefined ablation power and coolant flow rates for stick and track modes of operation. Such powers and flow rates can be used in the process of FIG. 11 to perform and/or guide predefined stick mode and track mode operations having ablation parameters tailored to the particular environment of the ablation needle.

Processes such as those described herein can leverage a system's ability to modulate the ablation zone size and shape by changing at least the coolant flow rate to perform a plurality of processes during an ablation procedure. Stick mode can be used to adhere an ablation needle to desired tissue so that the needle does not migrate prior to or during the treatment. Treatment ablation can then be provided to selectively denature target tissue. Finally, after completing the treatment, track mode ablation can be performed to reduce the risk of track seeding.

Processes described herein can be performed in systems including one or more ablation devices (e.g., microwave ablation needles). In an embodiment, a system is capable of operating three microwave ablation needles simultaneously. Such a system can be capable of performing treatment ablation process on all three needles simultaneously to control the volume of ablated tissue within the patient. In some examples, the system can be configured to perform processes described herein (e.g., stick mode operation or track mode operation) on a plurality of needles simultaneously and/or sequentially.

In an example process, to prepare to perform an ablation process using a plurality of needles, a user places a first needle in a desired location and performs a stick mode ablation process at the first needle. Subsequently, the user places a second needle in a desired location and performs a stick mode ablation process for the second needle. The process can be repeated until all needles are positioned as desired. Having adhered the previous needle(s) in the desired location(s) can prevent such needle(s) from moving undesirably while subsequent needles are placed.

Similarly, in an example process, after treatment ablation using a plurality of needles is complete, a track mode ablation process can be performed for each needle to reduce the risk of track seeding from the needles. The track mode process can be performed for each needle simultaneously or sequentially. Each needle can be removed after a track mode process is performed for that needle. In some examples, a track mode process is performed for each needle (simultaneously or sequentially), and then each needle is removed. In other examples, for each needle, a track mode is performed for that needle and the needle is removed prior to performing a track mode process for the remaining needles.

In some embodiments, coolant flow rate and applied ablation power are individually controllable for each of the ablation needles. Thus, each needle can be operated independently in individual modes of operation (e.g., stick mode), and the ablation parameters for one needle (e.g., coolant flow rate, ablation power) may be different from the other needles. In an alternate embodiment, the same coolant flow rate is provided to each needle (e.g., via a single motor operating a plurality of peristaltic pumps). In some such examples, various processes (e.g., stick mode, track mode) can be performed among all needles simultaneously, or can be performed individually, for example, by modulating the ablation power applied to the needles while providing the same coolant flow rate to each needle. For example, in an embodiment, the coolant is provided at the same flow rate to each of a plurality of needles, and stick mode processes are performed for each needle sequentially, wherein, needles not operating in stick mode have no ablation power provided thereto even though coolant is flowing therethrough.

While the invention is susceptible to various modifications and alternative forms, some specific embodiments thereof are shown by way of example in the drawings. The drawings may not be to scale.

The invention claimed is:
1. A microwave ablation method, comprising:
receiving a command to perform a first thermal ablation process;
providing coolant to a microwave ablation device at a first flow rate, an interior of a distal end portion of the microwave ablation device being fluidly isolated from an exterior of the distal end portion of the microwave ablation device so as to inhibit coolant leakage or tissue fluid penetration at the distal end portion;
applying ablation power at a first power level to the microwave ablation device;
stopping applying the ablation power at the first power level;
receiving a command to perform a second thermal ablation process after stopping applying the ablation power at the first power level;
providing the coolant to the microwave ablation device at a second flow rate; and
applying the ablation power at a second power level to the microwave ablation device,
wherein the first thermal ablation process is a stick mode ablation process or a track mode ablation process, the second thermal ablation process is a treatment ablation process, and the first flow rate is lower than the second flow rate.

2. The microwave ablation method of claim 1, wherein the first power level is lower than the second power level.

3. The microwave ablation method of claim 1, wherein the first power level equal to the second power level, such that an equal amount of the ablation power is applied to the microwave ablation device during the second thermal ablation process and the first thermal ablation process.

4. The microwave ablation method of claim 1, wherein the first power level and the second power level are in a range of 45-90 W.

5. The microwave ablation method of claim 1, wherein the second flow rate is at least 4 times larger than the first flow rate.

6. The microwave ablation method of claim 1, wherein the second flow rate is between 95 ml/min and 120 ml/min and the first flow rate is between 10 ml/min and 30 ml/min.

7. The microwave ablation method of claim 1, further comprising:
stopping applying the ablation power at the second power level;
receiving a command to perform a third process;
providing the coolant to the microwave ablation device at a third flow rate, the third flow rate being lower than the second flow rate; and
applying the ablation power to the microwave ablation device at a third power level.

8. The microwave ablation method of claim 7, wherein the third flow rate is lower than the first flow rate and the third power level is lower than the first power level and the second power level.

9. The microwave ablation method of claim 7, wherein the third flow rate is greater than the first flow rate, and the third power level is equal to the second power level.

10. The microwave ablation method of claim 7, wherein the third process comprises a track mode ablation process.

11. The microwave ablation method of claim 7, wherein the first thermal ablation process comprises the stick mode ablation process.

12. The microwave ablation method of claim 10, wherein performing the track mode ablation process comprises providing instructions, via a user interface, to remove the microwave ablation device from a medium while applying the ablation power to the microwave ablation device at the third power level and providing the coolant to the microwave ablation device at the third flow rate.

13. The microwave ablation method of claim 12, wherein providing the instructions to remove the microwave ablation device from the medium during or after applying the ablation power to the microwave ablation device at the third power level comprises providing instructions to remove the microwave ablation device at a predefined rate while providing the ablation power to the microwave ablation device at the third power level.

14. The microwave ablation method of claim 1, wherein the microwave ablation device is configured to perform both the stick mode ablation process and the track mode ablation process, and wherein the track mode ablation process is performed where the first flow rate is at a track ablation flow rate that causes a shape of ablation energy emitted from a needle to elongate along an axial direction of the needle and to narrow in a radial dimension of the needle.

15. A microwave ablation method comprising:
receiving a command to perform a track mode ablation process;
providing coolant to a microwave ablation device at a track mode flow rate, an interior of a distal end portion of the microwave ablation device being fluidly isolated from an exterior of the distal end portion of the microwave ablation device so as to inhibit coolant leakage or tissue fluid penetration at the distal end portion;
applying ablation power at a track mode power level to the microwave ablation device such that the coolant flows to the microwave ablation device during application of the ablation power so as to couple the application of the ablation power with the coolant flow; and
providing instructions for withdrawing the microwave ablation device from a medium;
wherein the track mode flow rate is greater than zero.

16. The microwave ablation method of claim 15, wherein providing the instructions to withdraw the microwave ablation device comprises providing instructions to withdraw the microwave ablation device from the medium at a prescribed rate.

17. The microwave ablation method of claim 15, further comprising:
receiving temperature information from a temperature sensor indicative of a temperature near the microwave ablation device; and
when the received temperature information satisfies a predetermined condition, stopping applying the ablation power to the microwave ablation device.

18. The microwave ablation method of claim 15, further comprising operating a pump during the application of the ablation power so as to cause the coolant to flow through the microwave ablation device during the application of the ablation power.

19. The microwave ablation method of claim 15, wherein the coupling of the application of the ablation power with the coolant flow influences a penetration depth of microwave energy into tissue proximate the microwave ablation device, wherein the coolant flow occurs at a first flow rate to generate a first ablation zone proximate to a needle, and wherein reducing the coolant flow results in at least one of:
increasing a coolant temperature of the coolant to thereby generate a second ablation zone that is smaller than the first ablation zone, and
reducing an ability of the microwave ablation device to draw heat away from the tissue proximate the microwave ablation device to thereby generate a third ablation zone with more localized heating of tissue proximate to the needle than the first ablation zone.

* * * * *